US012171529B2

(12) United States Patent
Ertin et al.

(10) Patent No.: US 12,171,529 B2
(45) Date of Patent: Dec. 24, 2024

(54) MOBILE ULTRAWIDEBAND RADAR FOR MONITORING THORACIC FLUID LEVELS AND CARDIO-RESPIRATORY FUNCTION

(71) Applicant: Ohio State Innovation Foundation, Columbus, OH (US)

(72) Inventors: Emre Ertin, Columbus, OH (US); William T. Abraham, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 782 days.

(21) Appl. No.: 17/260,827

(22) PCT Filed: Jul. 17, 2019

(86) PCT No.: PCT/US2019/042267
§ 371 (c)(1),
(2) Date: Jan. 15, 2021

(87) PCT Pub. No.: WO2020/018707
PCT Pub. Date: Jan. 23, 2020

(65) Prior Publication Data
US 2021/0290074 A1 Sep. 23, 2021

Related U.S. Application Data

(60) Provisional application No. 62/699,076, filed on Jul. 17, 2018.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0507* (2013.01); *A61B 5/0537* (2013.01);
(Continued)

(58) Field of Classification Search
None
See application file for complete search history.

(56) References Cited

U.S. PATENT DOCUMENTS 4,488,559 A * 12/1984 Iskander .............. A61B 5/103
600/548
5,986,602 A 11/1999 Frink
(Continued)

FOREIGN PATENT DOCUMENTS

CN 103245976 A 8/2013

OTHER PUBLICATIONS

Carcreff et all, "Resolution enhancement of ultrasonic signals by up-sampled sparse deconvolution", Oct. 21, 2013, IEEE pp. 1-5 (Year: 2013).*

(Continued)

*Primary Examiner* — Devin B Henson
*Assistant Examiner* — Matthew Eric Ogles
(74) *Attorney, Agent, or Firm* — Thomas | Horstemeyer, LLP

(57) ABSTRACT

Various examples related to mobile bodily monitoring using ultra-wideband radar are provided. In one example, a method for determining a bodily characteristic includes collecting sets of reflected backscatter data for a sequence of ultra-wideband (UWB) pulses transmitted via an UWB sensor, and a corresponding calibration measurement from a calibration channel; determining reflection coefficients for each tissue interface based on the sets of reflected backscatter data; and determining a fluid level content of the lung tissue based upon the reflection coefficients. The reflection coefficients can be determined from reflection profiles based upon the reflected backscatter data for that sequence of UWB pulses and the corresponding calibration measurement. The UWB sensor can include an array of transmit (Continued)

(TX) and receive (RX) antenna pairs positioned on a body of a user. The reflection profile can be associated with a model of tissue layers in the body between the UWB sensor and lung tissue.

15 Claims, 17 Drawing Sheets

(51) Int. Cl.
 *A61B 5/0507* (2021.01)
 *A61B 5/0537* (2021.01)
 *A61B 5/07* (2006.01)
(52) U.S. Cl.
 CPC .............. *A61B 5/07* (2013.01); *A61B 5/6833* (2013.01); *A61B 2560/0223* (2013.01)

(56) References Cited

U.S. PATENT DOCUMENTS

| | | | |
|---|---|---|---|
| 7,725,150 | B2 | 5/2010 | Tupin et al. |
| 8,428,696 | B2 | 4/2013 | Foo |
| 8,781,563 | B2 | 7/2014 | Foo |
| 9,002,427 | B2 | 4/2015 | Tupin et al. |
| 9,572,512 | B2 | 2/2017 | Weinstein et al. |
| 10,561,336 | B2 | 2/2020 | Rappaport et al. |
| 10,588,599 | B2 | 3/2020 | Weinstein et al. |
| 10,660,609 | B2 | 5/2020 | Weinstein et al. |
| 2003/0130711 | A1 | 7/2003 | Pearson |
| 2010/0256462 | A1 | 10/2010 | Rappaport et al. |
| 2011/0060215 | A1 | 3/2011 | Tupin, Jr. et al. |
| 2017/0156626 | A1* | 6/2017 | Kochba ................ A61B 5/0507 |
| 2017/0258366 | A1* | 9/2017 | Tupin, Jr. ............. A61B 5/6833 |

OTHER PUBLICATIONS

International Preliminary Report on Patentability issued in PCT/US2019/042267, dated Jan. 19, 2021 (10 pages).
Supplementary EP Search Report for PCT/US2019/042267, mailed Mar. 17, 2022.
Li, et al., "Ultra wideband radar for water detection in the human body", German Microwave Conference, Mar. 15, 2010.
Chinese Office Action for 201980058324.1 mailed Jul. 1, 2023.
Search Report and Written Opinion—Intellectual Property Office of Singapore; issued in app No. 11202100325X; mailed on Sep. 5, 2022.
Carcreff, et al., resolution enhancement of ultrasonic signals by up-sampled sparse deconvolution, Hall archives ouverts,Article on line 2013.
International Search Report filed Jul. 17, 2019 for PCT/US19/42267.
Israel Office Action for PCT/US2019/042267 mailed Dec. 11, 2023.
Carcreff, et al., "Resolution enhancement of ultrasonic signals by up-sampled sparse Deconvolution", HAL open science, IEEE International conference on acoustics, speech and signal processing May 2013.

* cited by examiner

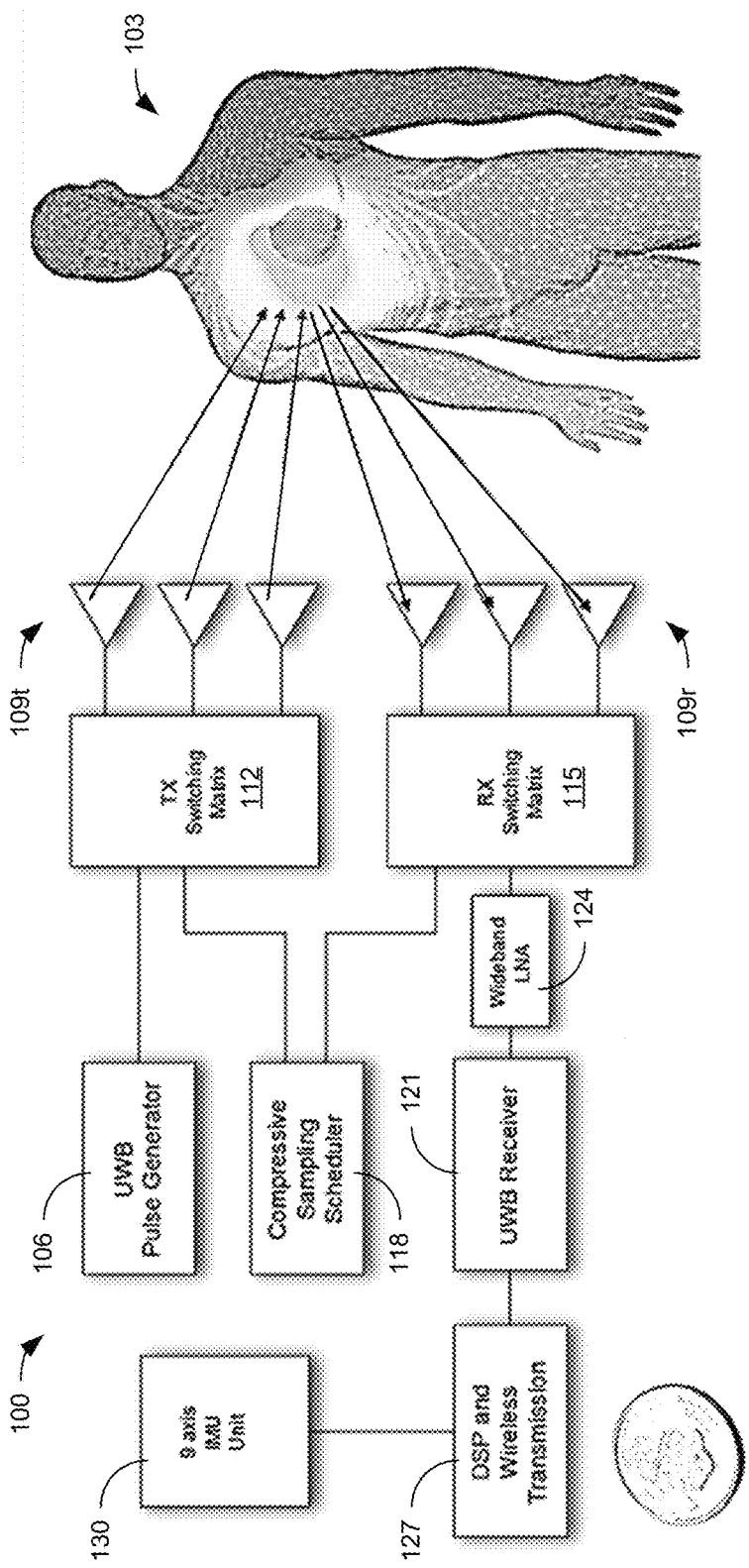
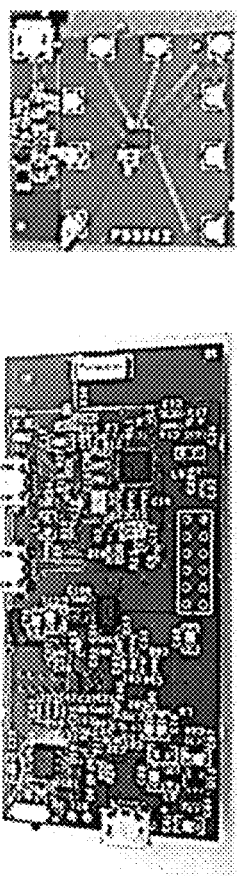
FIG. 1A  FIG. 1B  FIG. 1C

| Tissue | Loss Tangent | Relative Permittivity |
|---|---|---|
| Fat | 0.12 | 5.4 |
| Muscle | 0.32 | 54.8 |
| Lung | 0.38 | 21.8 |
| Body Fluid | 0.43 | 68.8 |
| Bone | 0.31 | 20.6 |

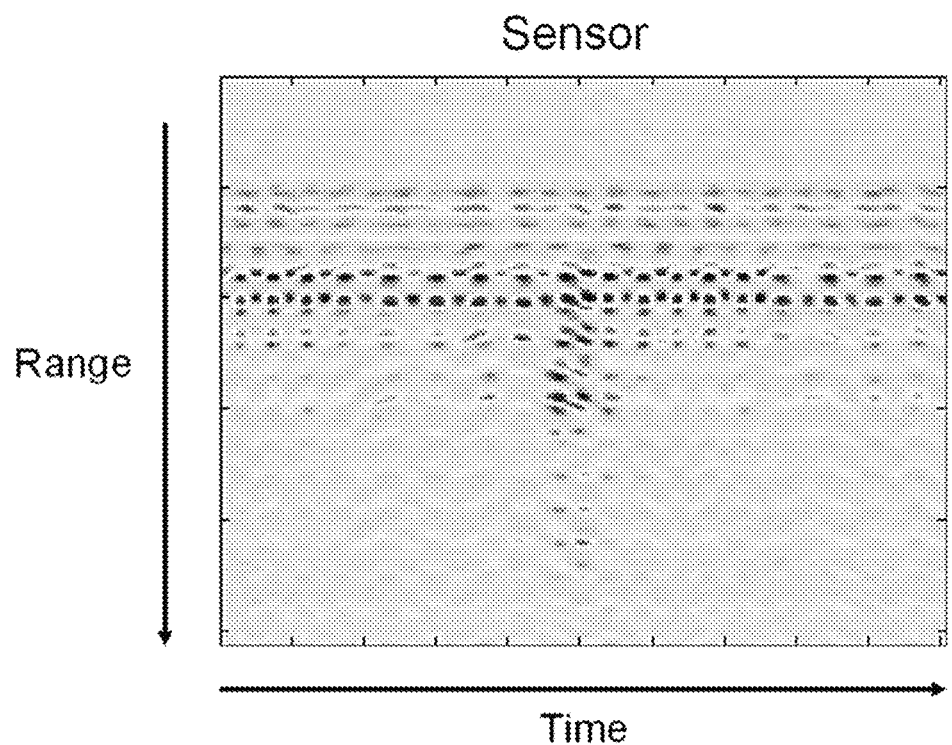
FIG. 4C
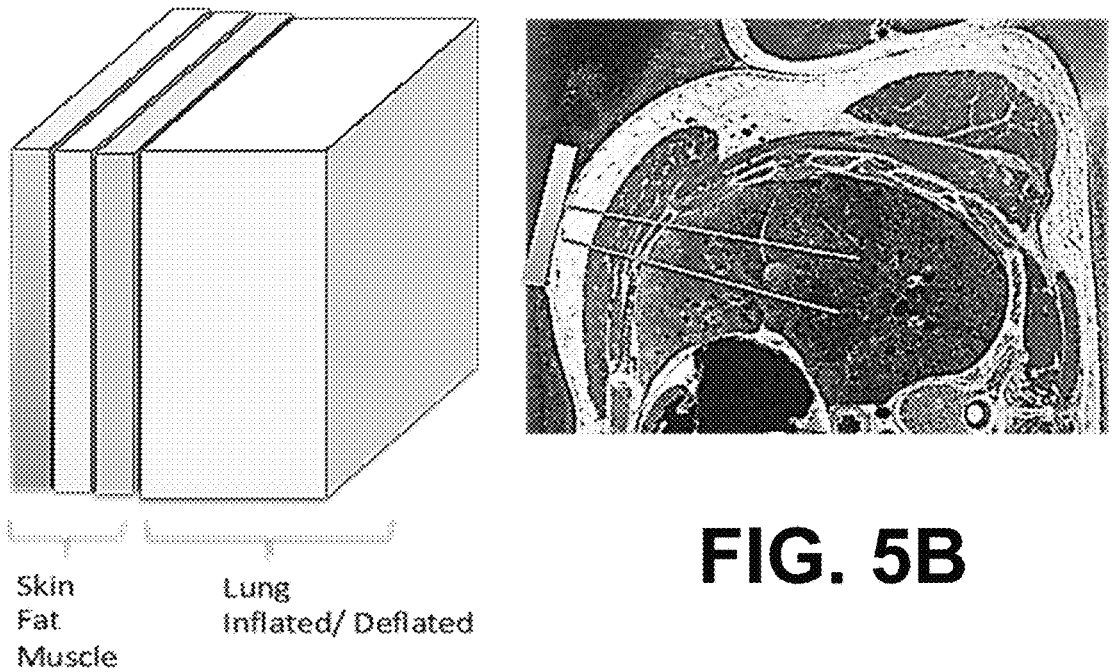
FIG. 5A
FIG. 5B

MOBILE ULTRAWIDEBAND RADAR FOR MONITORING THORACIC FLUID LEVELS AND CARDIO-RESPIRATORY FUNCTION

CROSS REFERENCE TO RELATED APPLICATIONS

This application is a National Stage of International Application No. PCT/US2019/042267, filed Jul. 17, 2019, which claims priority to, and the benefit of, U.S. provisional application entitled "Mobile Ultrawideband Radar for Monitoring Thoracic Fluid Levels and Cardio-Respiratory Function" having Ser. No. 62/699,076, filed Jul. 17, 2018, both of which are hereby incorporated by reference in their entireties.

STATEMENT REGARDING FEDERALLY SPONSORED RESEARCH OR DEVELOPMENT

This invention was made with government support under U54 EB020404 awarded by the National Institutes of Health and IIS1231577 awarded by the National Science Foundation. The Government has certain rights in the invention.

BACKGROUND

Congestive Heart Failure (CHF) affects nearly 6 million Americans, with 670,000 diagnosed annually. Heart failure is one of the leading causes of hospital admission and readmission and death in the United States (US) and is also one of the costliest disease syndromes, with direct and indirect costs of care estimated at $34.4 billion US dollars a year. About 80% of this high cost of care is related to managing episodes of heart failure decompensation in the hospital. Efforts need to be targeted towards improving heart failure outcomes and lowering costs of care. Earlier identification and treatment of worsening heart failure in the outpatient setting may prevent the development of heart failure exacerbations that lead to increased morbidity and hospitalizations. The current identifiers of worsening heart failure, namely weight gain and dyspnea, are unreliable and often develop too late in the timeline of diseases progression to change outcomes.

SUMMARY

Aspects of the present disclosure are related to systems, apparatus and methods for mobile bodily monitoring using ultra-wideband radar. In one aspect, among others, a method for determining a bodily characteristic, comprises collecting sets of reflected backscatter data for a sequence of ultra-wideband (UWB) pulses transmitted via an UWB sensor comprising an array of transmit (TX) and receive (RX) antenna pairs positioned on a body of a user, and a corresponding calibration measurement from a calibration channel in the UWB sensor; determining reflection coefficients for each tissue interface based on the sets of reflected backscatter data, the reflection coefficients determined from reflection profiles based upon the reflected backscatter data for that sequence of UWB pulses and the corresponding calibration measurement, the reflection profile associated with a model of tissue layers in the body between the UWB sensor and lung tissue; and determining a fluid level content of the lung tissue based upon the reflection coefficients.

In one or more aspects, the sets of reflected backscatter data can comprise reflected backscatter data obtained for each of the TX and RX antenna pairs in the UWB sensor that is combined to generate a wideband beamformed signal for each set of reflected backscatter data. The reflection profiles can be determined based upon sparse deconvolution of the wideband beamformed signal of that set of reflected backscatter data using a compensated UWB pulse shape that is based upon the corresponding calibration measurement. The sparse deconvolution of the wideband beamformed signal can be implemented for each of K frequency bands. In various aspects, the method can comprise identifying depth of a lung tissue interface at top (inhalation), middle and bottom (exhalation) points in a respiration cycle of the lung tissue based upon the reflection coefficients; and determining the fluid level content of the lung tissue can comprise determining fluid level content at the top, middle and bottom points in the respiration cycle. In some aspects, the method can comprise determining characteristics of tissue layers located between the UWB sensor and the lung tissue. The characteristics of the tissue layers can comprise location of at least one tissue layer interface or a dielectric property of at least one tissue layer.

In another embodiment, among others, a mobile bodily monitoring system comprises an ultra-wideband (UWB) sensor comprising an array of antennas comprising pairs of transmit (TX) and receive (RX) antennas, and a calibration channel, the UWB sensor configured to be positioned on a body of a user; a radio frequency (RF) front end comprising a UWB pulse generator coupled to the TX antennas of the array of antennas and a UWB receiver coupled to the RX antennas of the array of antennas, where UWB pulses generated by the UWB pulse generator are sequentially transmitted into the body of the user through the TX antennas and reflected backscatter signals are received through the RX antenna of that pair of TX and RX antennas; a wireless transmitter configured to communicate data associated with the reflected backscatter and a corresponding calibration measurement from the calibration channel; and a computing device configured to receive the data and determine bodily characteristics of the user based upon the reflected backscatter and corresponding calibration measurement.

In one or more aspects, the computing device can be configured to: determine a reflection profile based upon the data associated with the reflected backscatter and the corresponding calibration measurement for the sequence of transmitted UWB pulses, the reflection profile associated with a model of tissue layers in the body between the UWB sensor and a target tissue; determine reflection coefficients based upon the reflection profiles; and determine characteristics of the target tissue from the generated target tissue data. The characteristics of the target tissue can comprise depth of an interface with the target tissue or dielectric properties of the target tissue. The target tissue can be lung tissue. The computing device can be configured to identify a measure of lung fluid content based upon the characteristics of the lung tissue. The computing device can be configured to concurrently identify one or more of heart rate, heart rate variability, respiration rate or tidal volume. The computing device can be configured to identify top and bottom depths of a lung tissue interface over a respiration cycle of the lung tissue. The computing device can be configured to identify dielectric properties at the top and bottom depths and at an average depth in the respiration cycle of the lung tissue.

In various aspects, a reflection profile can be determined through sparse deconvolution of an averaged wideband backscatter signal based upon the data associated with the reflected backscatter for the sequence of UWB pulses. The computing device can be configured to determine reflection profiles for each of a series of reflected backscatter data sets, each of the reflected backscatter data sets comprising data associated with the reflected backscatter for the sequence of transmitted UWB pulses associated with that set. In some aspects, the calibration channel can comprise a temperature calibration loop having a load of known impedance positioned adjacent to the array of antennas. Variations in the transmitted UWB pulses can be compensated for based upon the corresponding calibration measurement. In one or more aspects, the mobile bodily monitoring system can comprise digital signal processing (DSP) circuitry configured to obtain and process the reflected backscatter signals and the corresponding calibration measurement for transmission to the computing device. In various aspects, the UWB pulses can be transmitted into the body at a rate of about 10,000 per second.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A is a schematic diagram illustrating an example of a mobile bodily monitoring system, in accordance with various embodiments of the present disclosure.

FIGS. 1B and 1C are images of portions of the mobile bodily monitoring system of FIG. 1A, in accordance with various embodiments of the present disclosure.

FIGS. 4A-4C illustrate backscatter responses of UWB pulses transmitted by the UWB sensor of FIGS. 2A-2F, in accordance with various embodiments of the present disclosure.

FIGS. 5A and 5B illustrate a multi-layer model and positioning of the UWB sensor of FIGS. 2A-2F, in accordance with various embodiments of the present disclosure.

DETAILED DESCRIPTION

Figure 2A:
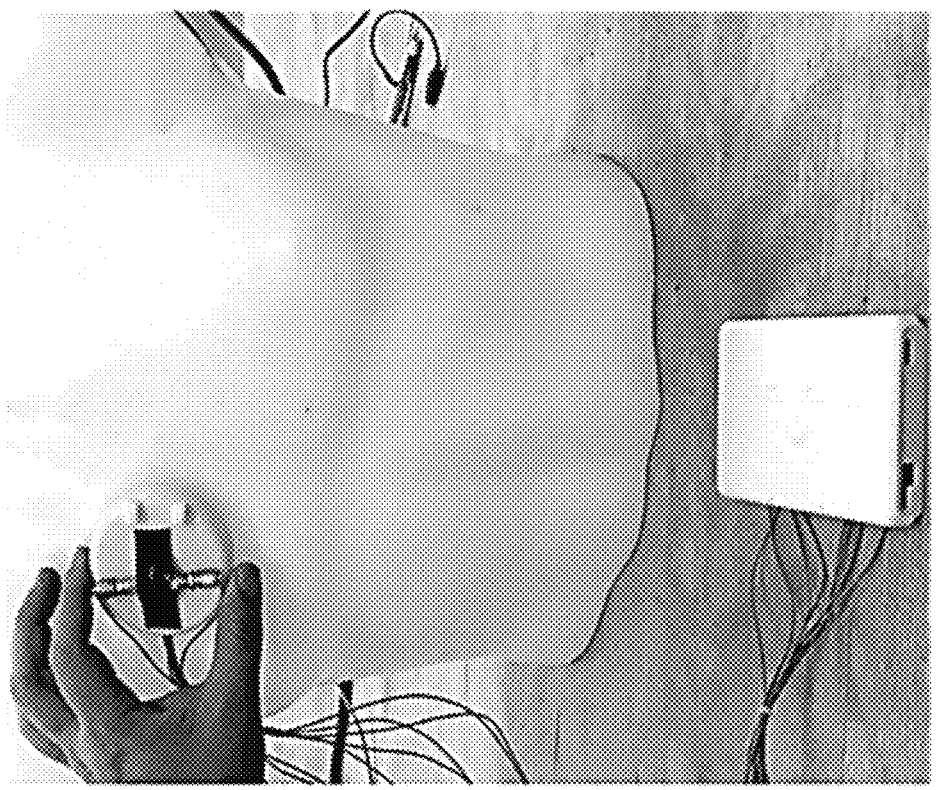
FIGS. 2A-2F illustrate examples of ultra-wideband (UWB) sensors of the bodily monitoring system of FIG. 1A, in accordance with various embodiments of the present disclosure.
Figure 2A:
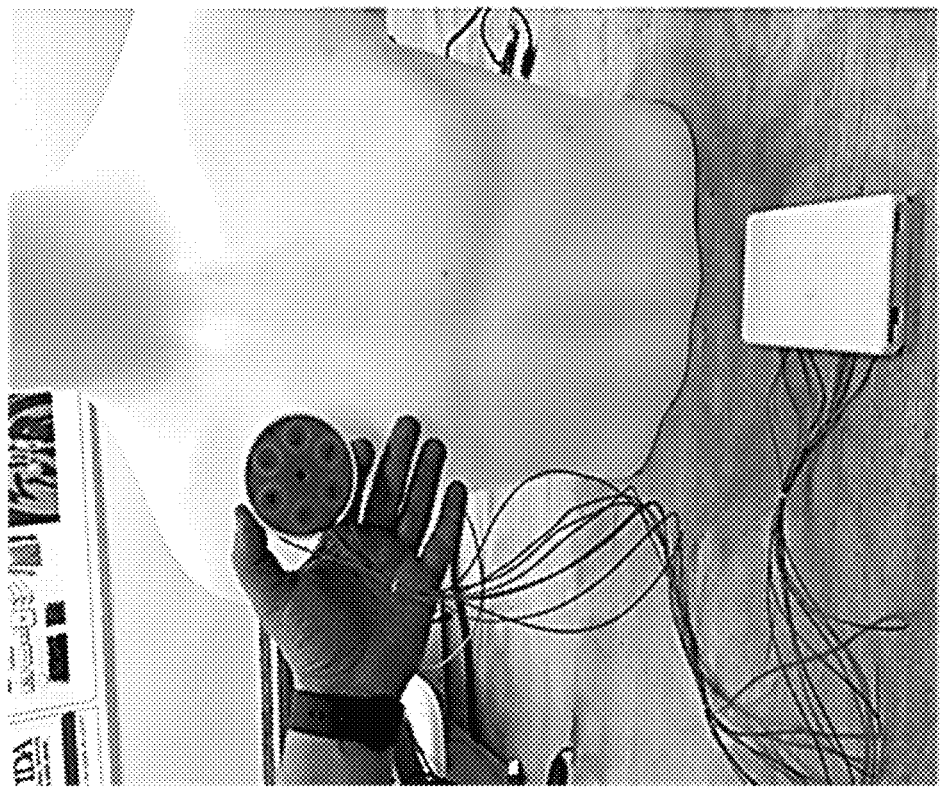

Disclosed herein are various examples related to systems, apparatus and methods for mobile bodily monitoring using ultra-wideband radar. Reference will now be made in detail to the description of the embodiments as illustrated in the drawings, wherein like reference numbers indicate like parts throughout the several views.

Technological advances in earlier detection of heart failure have revolved around measurements of transthoracic and intrathoracic impedance, since fluid accumulation develops prior to symptoms. The concept is based on electrical conductivity increasing with increased fluid and impedance correspondingly decreasing. Current methods like the OptiVol fluid index derived from implantable cardiac defibrillators (ICDs) have been helpful in measuring impedance invasively; yet, the accuracy in detecting pulmonary edema or predicting hospitalization has been quite variable. Another approach uses a dedicated implanted hemodynamic sensor to monitor pulmonary artery pressure. These approaches rely on information provided from implantable devices, whose applicability may be limited to all but the most advanced heart failure patients. Thus, there is a need for better non-invasive tools that can replicate the utility of these device-based diagnostic systems.

This disclosure presents a non-invasive technology developed for easy bodily sensing, which measures thoracic fluid levels, in addition to cardiac and lung motion by transmitting ultra-wideband radio frequency pulses and analyzing the backscattered waves. The bodily monitoring system can employ a single sensor unit placed anteriorly on the chest of a user to make its measurements. The sensor unit may be placed at other locations to determine other tissue characteristics. Unlike similar technologies, the mobile bodily monitoring system can be used to assess both quantity of fluid in thoracic tissue as well its spatial distribution, informing on intravascular and extravascular volumes; potentially clinically relevant measures. In addition, the fast acquisition speed of the bodily monitoring system allows tracking of cardiac and lung motion thus enabling continuous monitoring of heart rate, heart rate variability, respiration rate and tidal volume. The lung and heart measurements may be correlated to further evaluate the user's condition. These markers of cardiovascular system state used together with thoracic fluid levels can provide a comprehensive suite of measures that can be used to predict heart failure events with high sensitivity, low false alarm rate and sufficient lead time.

Referring to FIG. 1A, shown is a schematic diagram illustrating an example of a mobile bodily monitoring system 100, which may be controlled through a computing device interface such as, e.g., a smartphone interface. The bodily monitoring system 100 is an ultra-wideband (UWB) radar system that sends short pulses (e.g., 0.3-0.4 ns duration with an UWB of 0.5-3.5 GHZ) into the body of a user 103, and records the backscatter from the tissue. Radio frequency (RF) sensing is ideal for monitoring fine-grain internal motion due to its penetration capability into the tissues. Each tissue interface at, e.g., the air/skin, skin/fat, fat/muscle, and/or muscle/lung transitions provides a reflection point that can be tracked in real time through processing of the backscatter echo signals.

The mobile bodily monitoring system 100 can utilize a low power, micro UWB platform to detect the backscatter energy reflected by the tissue and its transitions, and measure heart and lung motion, and determine other bodily characteristics such as thoracic fluid levels, which can be used in the detection of congestion in CHF. As shown in FIG. 1A, the mobile bodily monitoring system 100 can include an UWB pulse generator 106 that generates one or more UWB pulse transmitted into the tissue of the user 103 by antennas 109$t$ coupled through transmit (TX) switching matrix 112. For example, the UWB pulse generator 106 can generate the UWB pulses with 0.45-3.55 GHz operation. The backscatter from the tissue interfaces is received by antennas 109$r$ coupled to receive (RX) switching matrix 115. The RX switching matrix 115 directs the received backscatter signal to an UWB receiver 121 through a wideband low noise amplifier (LNA) 124. A compressive sampling scheduler 118 can coordinate the switching between the different antennas 109 for transmission of the UWB radar pulse and reception of the backscatter. Multiple input/multiple output (MIMO) diversity can be used to focus the signals on the sources of motion, or areas of interest. FIG. 1B is an image showing an example of a platform for the TX switching matrix 112 and the RX switching matrix 115 to couple with the antennas 109.

Digital signal processing (DSP) and wireless transmission circuitry 127 can process the backscatter signals and wirelessly transmit (e.g., via Bluetooth®, WLAN, or other appropriate wireless link) the signal data to a separate computing device such as, but not limited to, a computer, smartphone, tablet or other mobile processing unit for subsequent processing. The DSP circuitry 127 can compress or otherwise process the backscatter signals for efficient transmission of the data. An inertial measurement unit (IMU) 130 can also provide orientation and/or movement information to the DSP circuitry 127, which can also be transmitted to the separate processing unit. FIG. 1B is an image showing an example of the UWB platform, with a quarter to illustrate its overall size.

Figure 2B:
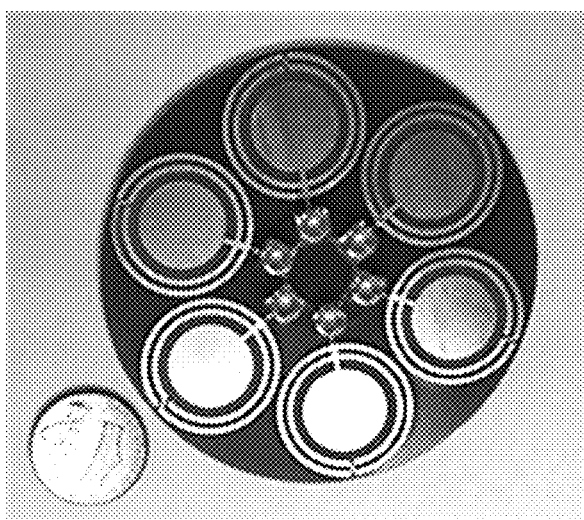
Figure 2D:
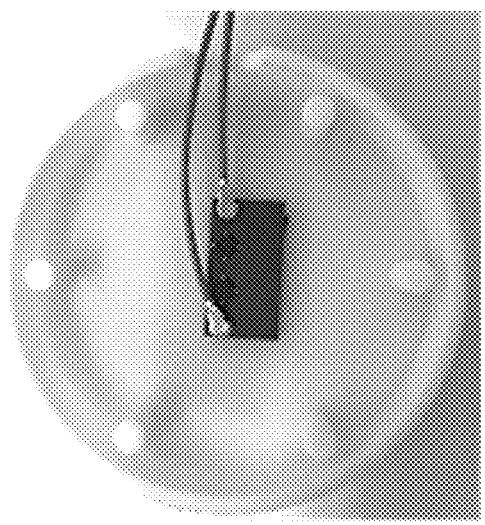
Figure 2C:
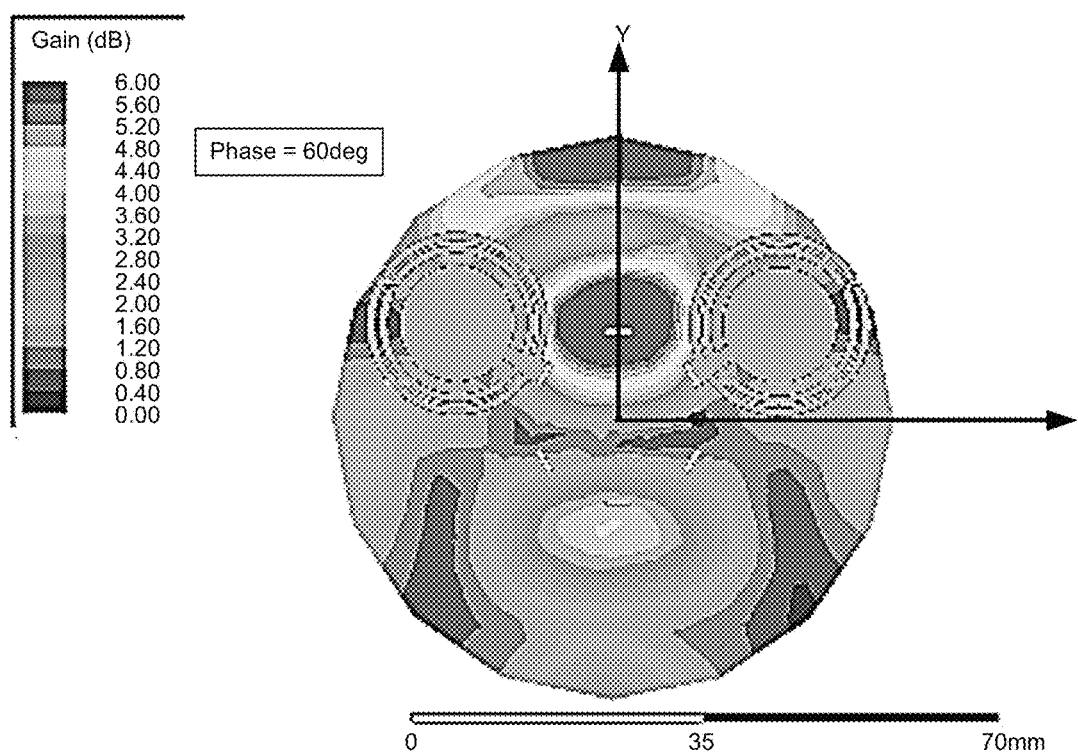

Referring next to FIG. 2A, shown are images of an example of a mobile bodily monitoring system 100 including an UWB RF sensor having a circular array of antennas 109. As illustrated in FIG. 2A, the UWB RF sensor can be positioned on the user's chest with the array of antennas adjacent to the skin to direct the transmitted UWB pulse into the tissues and receive the reflected backscatter. Placement of the UWB RF sensor can be facilitated through, e.g., an interface on the computing device (e.g., smart phone, tablet or other mobile device). The sensor can be held to the user's chest and calibration initiated through the interface. Feedback can be provided to the user to adjust the position of the sensor if necessary to provide adequate coupling with the bodily tissue. An array of N-pairs of antennas can be designed to have a good impedance match over the wide band of frequencies of interest. The design can optimize the phase center so that electromagnetic (EM) transmission occurs at the midpoint of the transmit antenna for each frequency band, to ensure that all frequency bands look at the same tissue composition (e.g., thickness, etc.). FIG. 2B is an image of the circular array including 6 pairs of antennas 109, and FIG. 2C illustrates an example of a radiation pattern of the TX antenna centered launch of EM waves. The TX and RX pairs of antennas 109 can be averaged to find a one dimensional (1D) cut through the tissues. Larger linear or planar arrays can be used to make 2D and 3D images of the tissues (e.g., fat, skin, muscle, bone, lung, etc.) under observation.

The measurements of the backscatter signals are sensitive to small variations in the hardware due to temperature and other environmental effects over time. To compensate for these effects, the UWB RF sensor can include a calibration channel (or loop) in communication with the DSP and wireless transmission circuitry 127. The calibration channel includes a load of known impedance positioned adjacent to the array of antennas, which is used to obtain loopback measurements that are used to calibrate for variations in the transmitted pulse including its timing with respect to the digital trigger. FIG. 2D is an image showing the load positioned on the casing of the UWB RF sensor, which is adjacent to the antennas 109 when assembled. The loopback signal is processed to extract an instantaneous estimate of the transmitted pulse and its timing with respect to the trigger, which in turn can be used in estimating tissue profiles from the backscatter echo of that transmitted pulse.

Figure 2E:
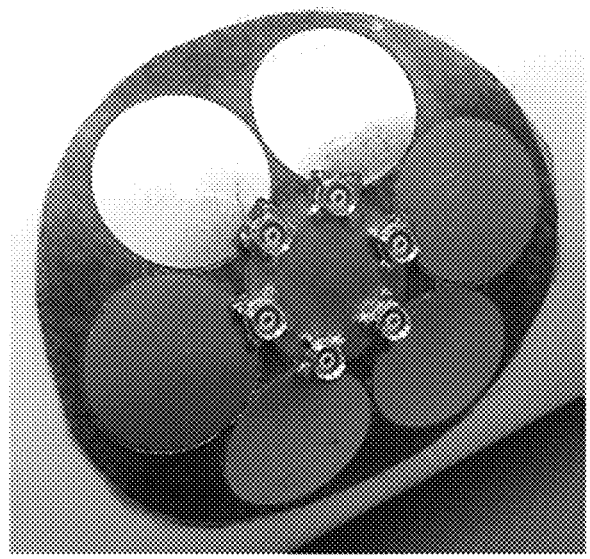
Figure 2F:
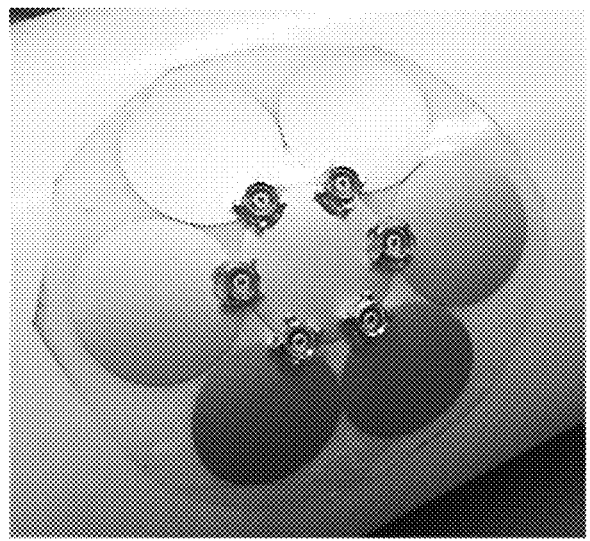

FIGS. 2E and 2F are images of flexible circular arrays including 6 pairs of antennas 109, which may be used as an ergonomic conformal UWB RF sensor. The UWB RF sensor can be positioned on the user's chest with the array of antennas secured to the skin (e.g., using an adhesive patch) to direct the transmitted UWB pulse into the tissues and receive the reflected backscatter. Placement of the UWB RF sensor may be facilitated through, e.g., an interface on the computing device (e.g., smart phone, tablet or other mobile device). The sensor can be positioned on the user's chest and calibration initiated through the interface. Feedback can be provided to the user to adjust the position of the sensor if necessary to provide adequate coupling with the bodily tissue. An array of N-pairs of antennas can be designed to have a good impedance match over the wide band of frequencies of interest. The ergonomic RF patches of FIGS. 2E and 2F integrate antenna elements 109 on a flexible substrate that can easily be applied anteriorly on, e.g., the right chest of the user and removed after measurements have been obtained. Connectors allow for coupling to each of the antennas 109. For example, the RF electronic circuitry and digital backend cam be located in a sensor pod that connects to the flexible antenna array using low profile RF connectors. Switching circuitry (e.g., the TX switching matrix 112 and the RX switching matrix 115) and/or UWB pulse generator and sampler can also be integrated onto the substrate or can be provided as part of a connector assembly for coupling to the connectors for the antennas 109. Digital signal processing (DSP) and wireless transmission circuitry 127 can also be integrated onto the substrate. This can allow for real-time, point-of-care lung water measurements and lung water fluid estimation through software (and/or firmware) implemented by the DSP or other integrated processing circuitry.

To couple and focus the RF energy into the body, an antenna array comprising patch antennas counterpoised with a center ground plane can be used. As illustrated in the example of FIGS. 2E and 2F, six circular patches can be arranged around a circular ground in alternating transmit-receive pairs. While the technology does not require skin contact, implementing the antenna array on a flexible substrate in the form of a light adhesive patch can support a robust consistent placement method without needing external support means such as a vest or harness. An RF patch antenna made of controlled dielectrics can eliminate the air gap and minimize the first reflection from the skin, thus increasing the dynamic range of the measurements.

FIGS. 2A and 2B illustrate two examples for implementing the antenna array on a flexible substrate, which can also integrate electronic components (or circuitry) of, e.g., the switching matrices and radar chip set. FIG. 2A shows flexible RF laminates with ceramic cores and copper surfaces. These flexible laminates can be processed in a subtractive process where a milling machine is used to remove copper to create the antenna surfaces, signal traces and pads for integrated circuits (ICs). Standard flow soldering can be applied to integrate the electronic components onto the antenna patch. This technology makes integration of electronic components easy, allowing designs that combine multilayer rigid IC boards or chips soldered to the flexible two layer substrate.

FIG. 2B shows screen printing of silver ink on polyester film to form the antennas. Silver ink has excellent conductivity and allows printed boards to be created in an additive manner, with conductive ink and insulating layers deposited on polyester film. This process is low cost and allows for the formation of multilayer structures (e.g., signal traces and antenna patches), however integrating components is more difficult as standard alloys used in soldering do not adhere to the conductive ink and the polyester substrate is heat sensitive. Therefore conductive epoxy adhesive is used to attach connectors and components. Also conductive ink may become brittle, limiting amount of shear stress and torsion that can be applied to the patch. However, these may not be an issue for single or limited use applications.

As shown in the images of FIGS. 2A and 2B, prototype versions of antenna arrays have been manufactured (without integrated electronic circuitry) using both processes. The ability of the antenna array to couple energy into the body have been characterized in each case using a network analyzer. Both designs provide good impedance matching and gain over the wide band of frequencies (e.g., 0.5 GHZ-3.5 GHZ) used by the system. In various implementations, the radar chipsets can be integrated to the antenna layer with an adhesive conformal RF patch that can be attached anteriorly on the right front chest. A small sensor pod can include the digital backend, battery and a Bluetooth® transceiver that attaches to the RF patch using, e.g., a self-guiding magnetic connector that will power the RF patch and obtain the measurements. To allow patients and the care givers to assess fluid status levels in real-time at home as well as at point-of-care (POC) settings, the lung fluid estimation technique can be implemented within the sensor device or sensor bode, with a wireless interface on a mobile device for control and storage. To provide real time POC measurements without cloud connectivity, a processor may be built into the sensor (e.g., an ARM Cortex M4F) to implement the analysis. This can streamline the data path from the sensor to a smart phone, tablet or other mobile device and minimize the data rate and associated latency.

Figures 3A, 3B:
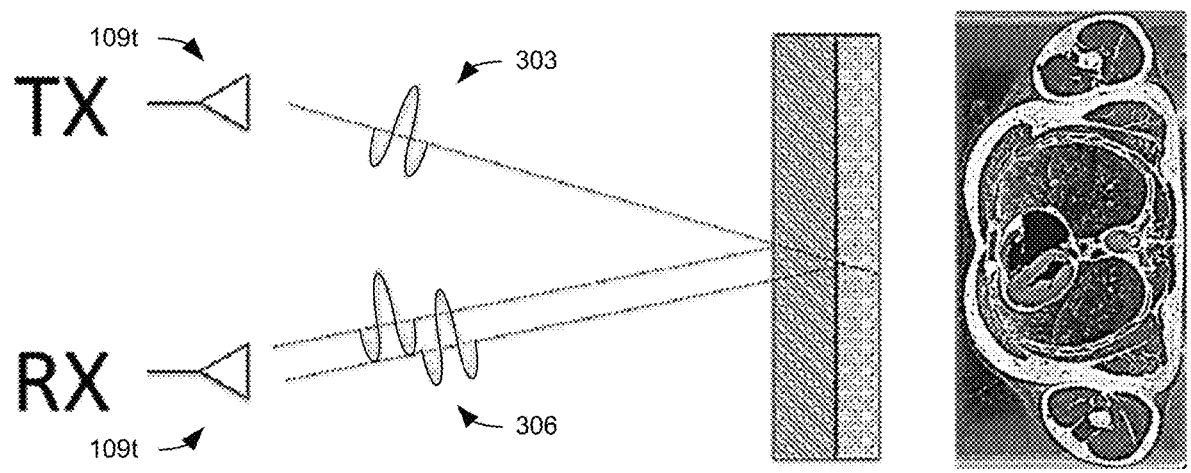
FIGS. 3A and 3B illustrate sensing of the tissues using the UWB sensor of FIGS. 2A-2F, in accordance with various embodiments of the present disclosure.

FIG. 3A illustrates the sensing of the tissues using the TX and RX antenna pairs 109. An UWB radar pulse 303 can be launched into a body from a TX antenna 109$t$ coupled through the TX switching matrix 112 of FIG. 1A. As the UWB pulse 303 propagates through the tissues of the body, backscatter 306 from the tissue interfaces is reflected back to the RX antenna 109$r$. As can be seen in the cross-sectional image of FIG. 1A, the human body is made of various tissues of differing dielectric properties which affect the UWB pulse 303 and backscatter 306 as it propagates through the body. For example, the relative permittivity influences the propagation delay through the tissue and the loss tangent affects the absorption of RF energy by the tissue. As can be seen, there exist multiple tissue interfaces for different layers of, e.g., skin, fat, muscle, bone, lung, etc. The table of FIG. 3B provides examples of the loss tangent and relative permittivity of some of the tissues. The backscatter reflected back to and received by the RX antenna 109$r$ include these overlapping returns, which can be processed to resolve the location of the various tissue interfaces, and associated complex reflection coefficients, revealing the characteristics of the tissues that make up the interface. The high bandwidth and narrow duration (e.g., 0.3-0.4 ns) of the UWB pulses allows for higher spatial resolution than, e.g., Doppler radar and enables gating of the returns to the tissue depth of interest.

Figure 4A:
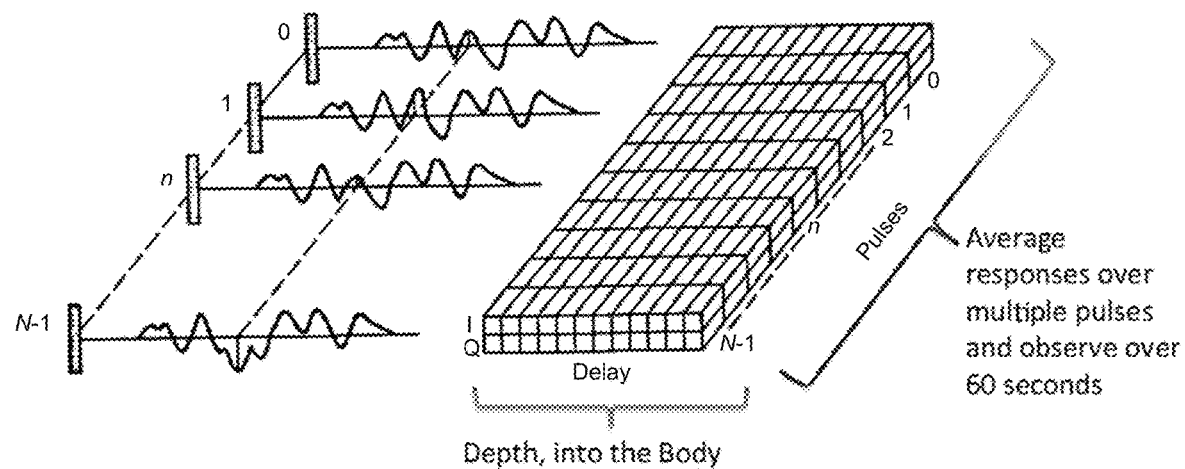

During operation of the mobile bodily monitoring system 100, thousands of pulses per second (e.g., 10,000 per sec) can be sent from the TX antenna 106$t$. Each pulse return contains several echoes delayed in time indicating depth into the body. As illustrated in FIG. 4A (Radar Principles, N. Levanon, 1988), the backscatter responses include returns from different depths (or ranges), which can be averaged over short time periods (e.g., every 0.1 second) or intervals (e.g., every 100 pulses). Considering that a 60 second interval encompasses 15-20 respiration cycles, averaging the responses over such short time periods enhances the return signal to noise ratio without sacrificing the depth information. In this way, the bodily monitoring system 100 provides 1-D echoes through the tissues several times during the respiration cycle.

Figure 4B:
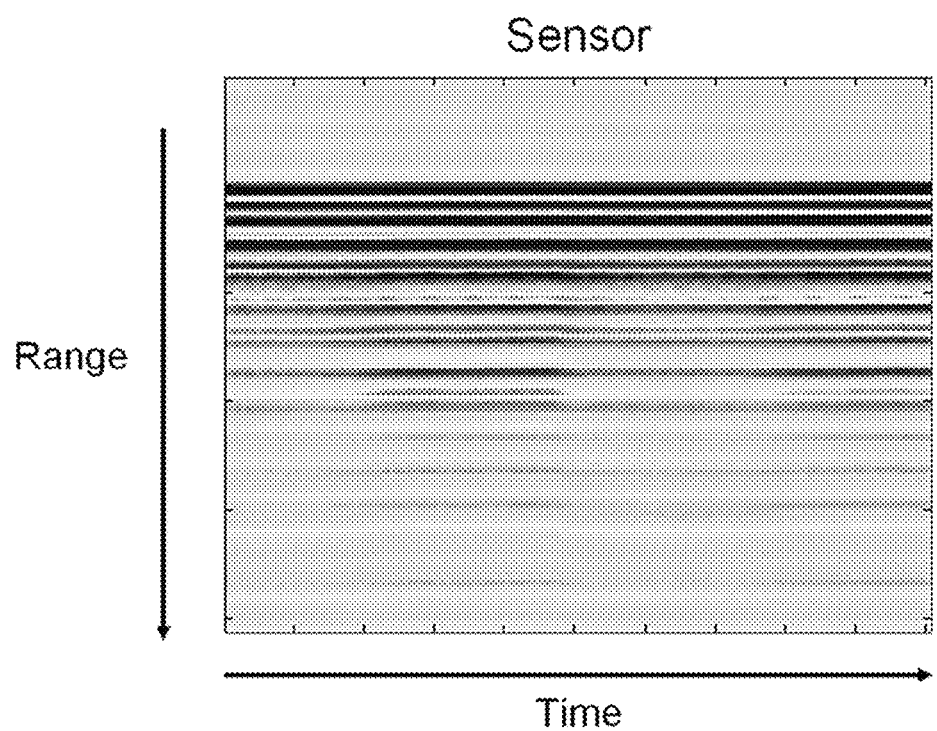

In some embodiments, the bodily monitoring system 100 can process the backscatter signals to produce range profiles at a 100 Hz rate. As illustrated in FIG. 4B, each range profile can indicate the position of the reflection boundaries when convolved with the transmitted pulse shape. Filtering the signal over pulses for frequencies consistent with heart motion (e.g., 0.5-2 Hz) and/or lung motion (e.g., 0.1-0.3 Hz) reveals structure as shown in FIG. 4C.

The properties of the skin, fat, muscle, lung and/or other tissue are modeled and estimated in order to estimate the permittivity of the lung tissue that can be used to determine lung water or fluid content. Considering a multi-layer model for the tissues through which the EM waves propagate (e.g., skin, fat, and muscle), such as the one illustrated in FIG. 5A, the lung parameters (e.g., thickness and composition) can be estimated. FIG. 5B shows an example of the positioning of the UWB RF sensor on the chest of the user and illustrates the propagation path of the UWB pulses into the body. The reflection/transmission coefficient for the lung tissue can be estimated using the wideband measurements from the reflected radar pulses (0.5-3.5 Ghz) and the estimated multi-layer EM propagation model for the tissues between the UWB RF sensor and the lung. Since the lung tissue dielectric properties change during the respiration cycle, the lung tissue dielectric properties are estimated at the three points in the respiration cycle (at the bottom of exhalation, at the top of inhalation and at the middle (or average) of the respiration cycle) for overall evaluation of the lung tissue.

The mathematical model for the interface (e.g., skin, fat, muscle and/or bone) is non-parametric and can be learned from the sensor data itself with no prior information on the thickness and order of the tissues. Assuming that there are K layers between the UWB RF sensor and the lung tissue (e.g., K=3 or K=4), the thickness and permittivity of each layer can be estimated, assuming an average value for the loss tangent. Since these parameters can be frequency dependent, the sensor measurements can be divided into M frequency bands with a width of, e.g., 500 MHz over which the tissue properties can be assumed to be constant. The returns from multiple TX and RX antenna pairs can then be combined for each band and corrected for drifts in the trigger delay using the measurement from the calibration channel (or loop). The calibration measurement can be used to account for distortion and delay produced by the hardware, but does not account for the transmission interface between the antenna pairs and the body. This transmission function be accounted for using a system model.

Figure 6:
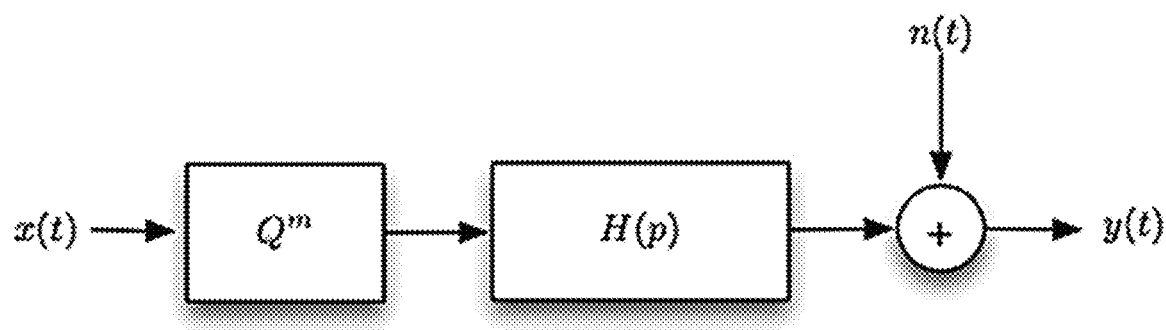
FIG. 6 is a schematic diagram illustrating an example of a system imaging model, in accordance with various embodiments of the present disclosure.

FIG. 6 is a schematic diagram illustrating an example of a system model for the RF imaging. The model can be expressed as:

$$y_i^m = G^m H(p_i) Q^m x_i + n_i$$

where $y_i$ is the radar return (or backscatter) for frame i, $x_i$ is the estimated reflection (or reflectivity) profile for frame i, p(t) is the impulse response of the radar, $Q^m$ is the bistatic projection matrix for the m-th channel, and H(p) is Toeplitz structured matrix representing the convolution with the transmitted pulse $p_i$, $G^m$ is the antenna/body transfer function. Similarly, the reference channel response can be represented as:

$$r_i = H(p_i) z_i + n_i$$

First, sparse deconvolution inversion algorithm (or other regularized inversion) can be used to invert the reference channel to get an estimate of the transmitted pulse, in the presence of temperature and other environmental factors, enforcing constraints on the power and band limited frequency support and using l1-norm to enforce the sparse set of reflections in the reference channel (ideally a single reflection, but in practice a few due to the imperfect connector mismatches)

$$\min_{\{p_i, y_i\}} |z_i|_1 \text{ s.t. } |r_i - H(p_i)z_i|_2 \le \sigma_{ref}^2 \quad |p_i|_2 \le 1 \quad \sum_l p_i(l) e^{(-j\omega l)} = 0$$

outside passband While sparse deconvolution inversion is used here to sharpen the reflection profiles, other regularized inversion methods may also be utilized to achieve this result. For example, regularized inversion methods such as Tikhonov regularization, TV (total variation) norm regularization, Lp norm regularization and Machine Learning based inversion methods such as generative adverserial networks, or deep neural networks can be used to sharpen the range profiles. Next, the estimated pulse $\hat{p}_i$ from the reference channel can be used to estimate a sparse set of reflectors corresponding to the tissue interfaces and the antenna transfer function. The mixed L21-norm imposes group sparsity, encoding the knowledge that over a short time frame the tissue boundary locations are stationary with respect to the range bins, but their complex amplitudes may vary based on respiration and other internal motion.

$$\min_{\{G, x_i\}} |\{x_1^m, \ldots, x_N^m\}|_{2,1} \text{ s.t. } |y_i^m - G^m H(\hat{p}_i) x_i^m|_2 \le \sigma_{mes}^2, G^m$$

is unit power and bandlimited It should be noted that due to internal reflections a K layer model will produce in general a number of distinct returns larger than K. The tissue/fluid estimation can focus only on the first return from each tissue interface.

The solution to both optimization problems can be achieved by alternating the minimization of multiple convex problems corresponding to the various constraints and result in absolute measurements of the complex reflection coefficients $\{x_1^m, \ldots, x_N^m\}$, implementing a wideband (over 3 GHz bandwidth in our case) calibration against pulse distortions as well as against antenna transfer function variations due to replacement and body detuning the antenna.

Figure 7A:
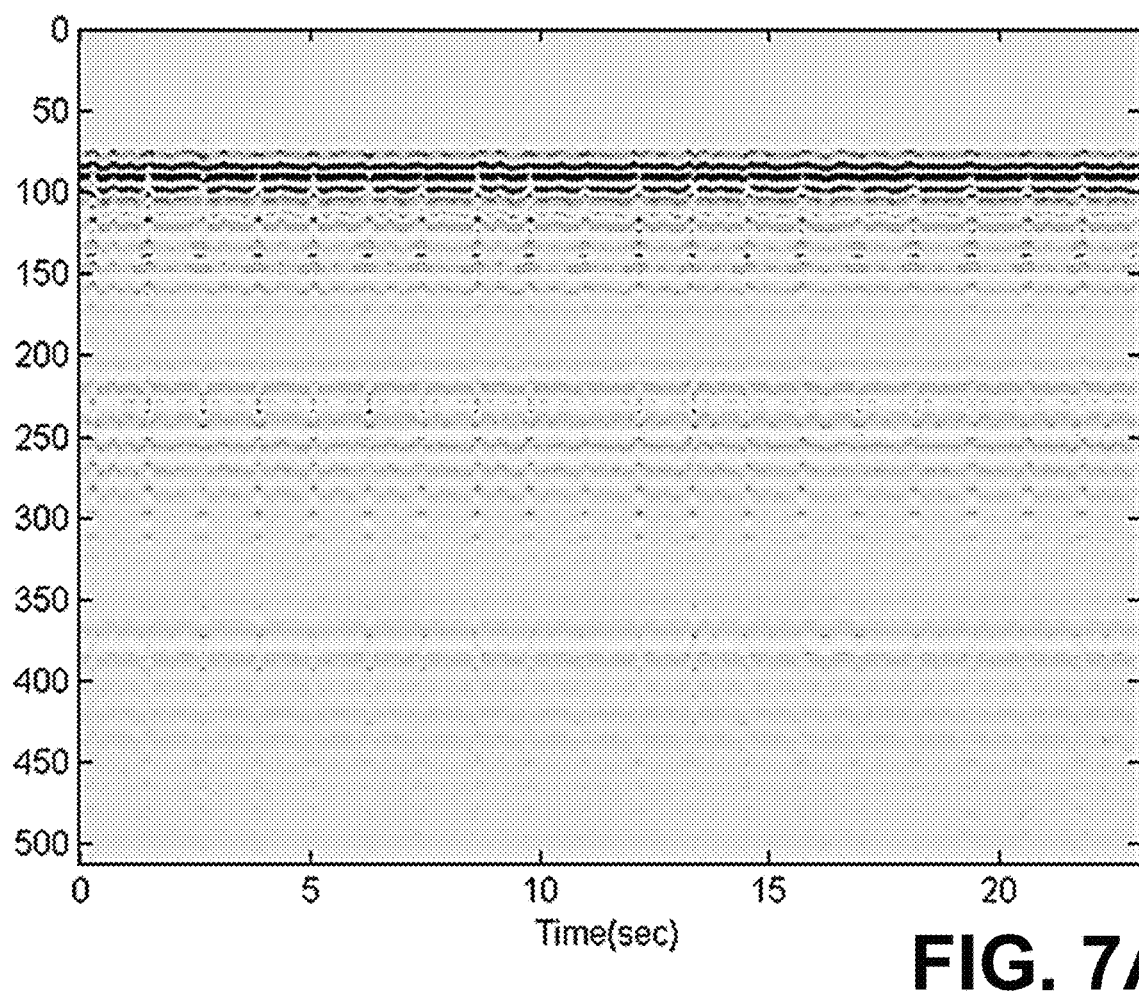
FIGS. 7A-7C illustrate examples of measured backscatter data, recovered sparse reflection profile and learned pulse shape, in accordance with various embodiments of the present disclosure.
Figure 7B:
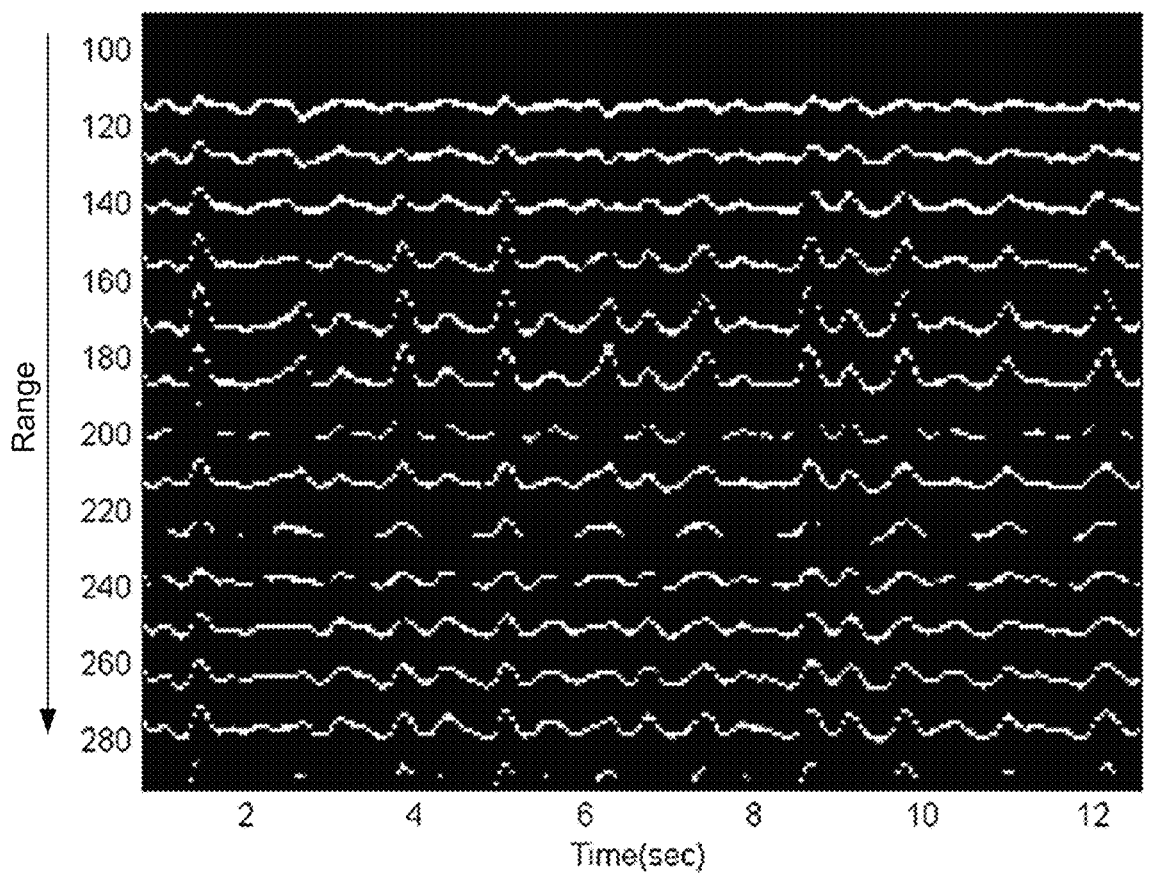
Figure 7C:
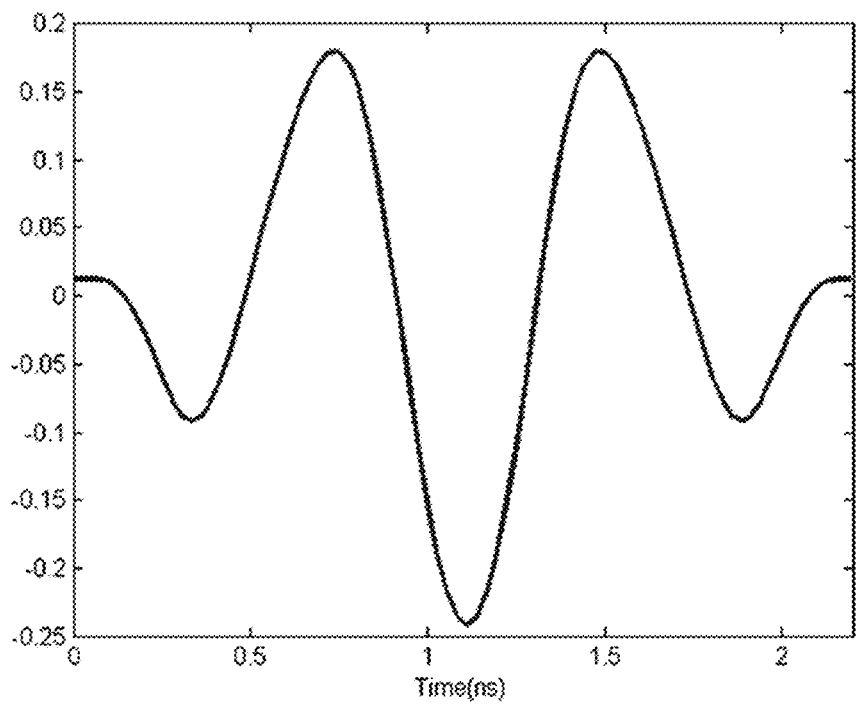

FIG. 7A shows an example of measured backscatter data, and FIGS. 7B and 7C show the recovered sparse reflection profile and learned pulse shape, respectively. The determination of the reflection profile can be greatly improved by using the loopback measurements from the calibration circuit to adjust for distortion and delay in the transmitted response.

Figure 8A:
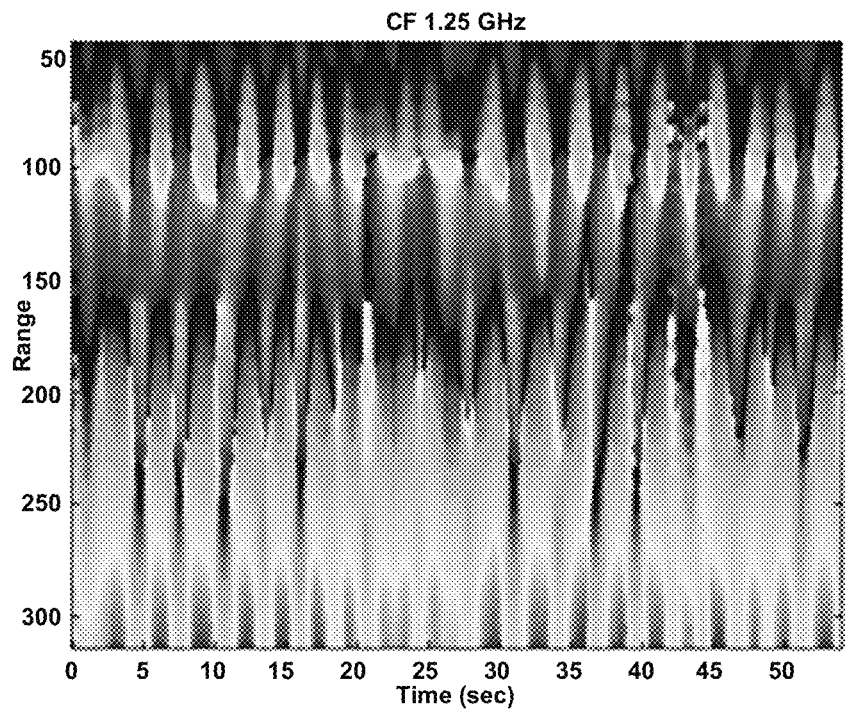
FIGS. 8A and 8B illustrate examples of frequency bands of backscatter data, in accordance with various embodiments of the present disclosure.
Figure 8B:
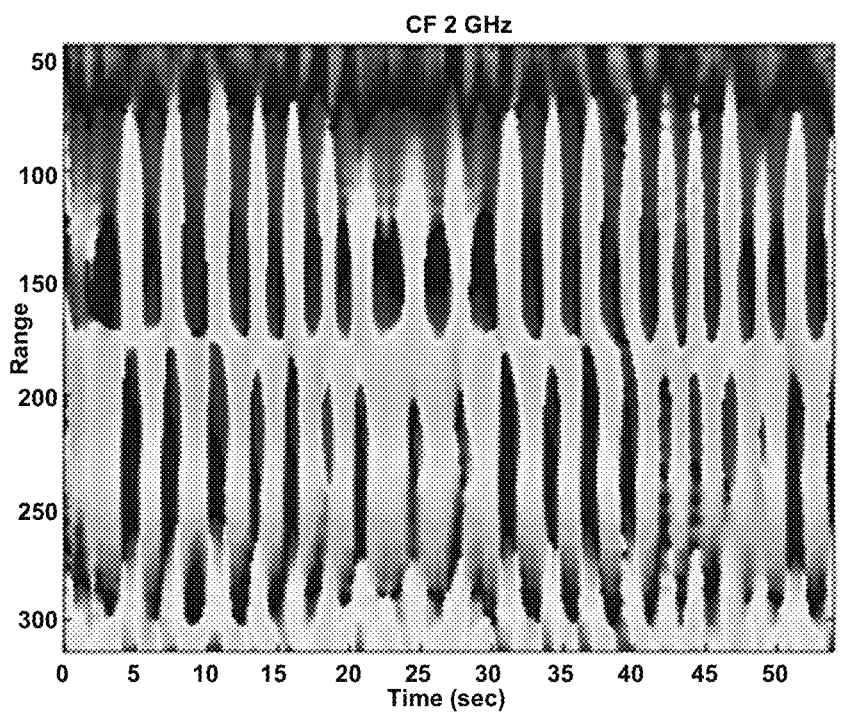

For example, the returns from two frequency bands are given in FIGS. 8A and 8B, with center frequencies of 1.25 GHZ and 2 GHz respectively. The depth (or range) into the body is given on the y-axis and the time over respiration cycles is on the x-axis. Different points on the respiration cycle and average returns can be identified for the top, bottom and middle of the respiration cycle over the respiration periods in one minute.

Figure 9A:
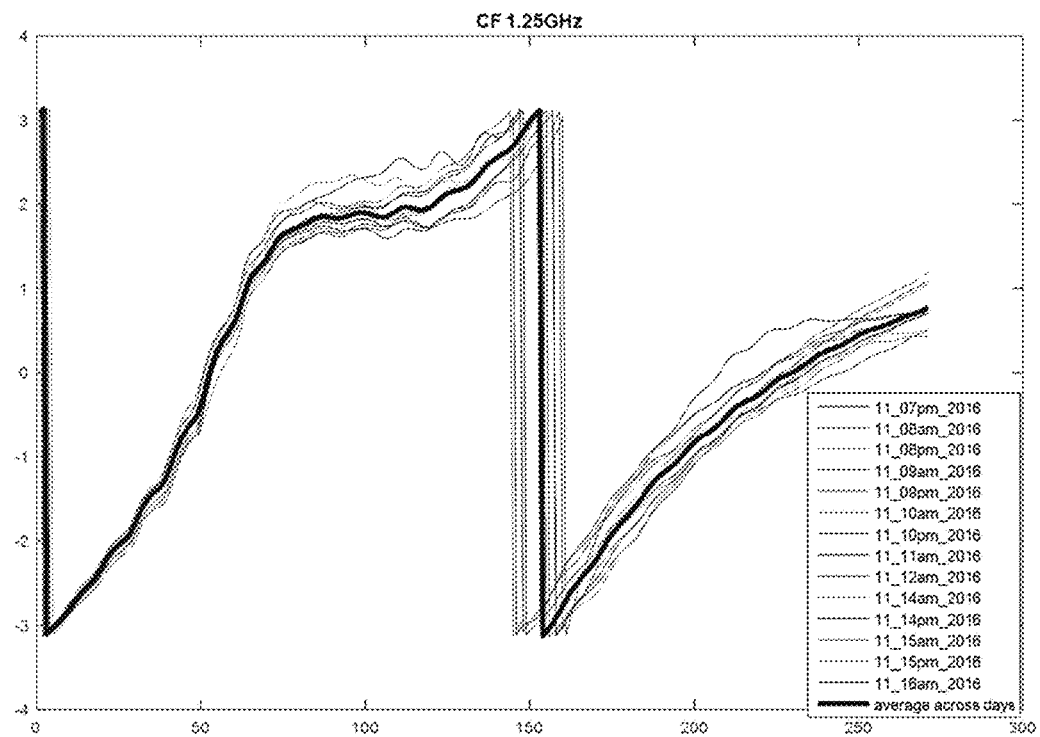
FIGS. 9A and 9B illustrate examples of phase returns processed from the backscatter data, in accordance with various embodiments of the present disclosure.
Figure 9B:
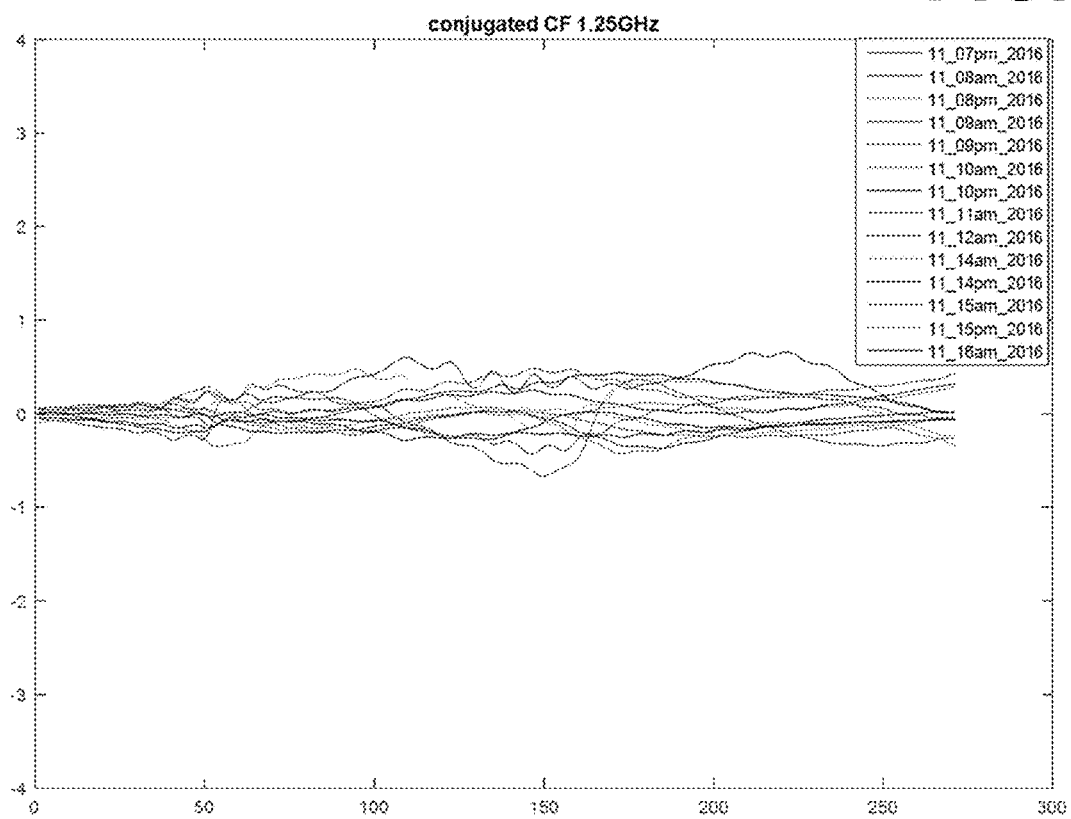

Then, the effect of the multi-layer tissue model (including, e.g., skin, fat, muscle and/or bone) can be estimated and removed from the measurements, leaving only the reflection and transmission of the lung tissue returns. FIG. 9A shows the phase returns from all tissues, and FIG. 9B illustrates the removing effect of the interface (e.g., skin, fat, muscle and/or bone).

Next, reflection coefficients can be determined from the reflection profile, and the lung response across the depths (or ranges) corresponding to the lung content can be aggregated to provide a measure of lung water or fluid content. It should be noted that because of the propagation delays through the tissues and the interface locations, the reflection coefficients are complex values including both magnitude and phase information about the backscatter signals. The backscatter based monitoring system is unique in its ability to resolve the tissues based on the delay and therefore can inform where (in which tissues) the change in fluid volume occurs in addition to the quantity of fluid. This is not possible with alternative systems that use pass-through measurements using transmitter and receivers placed posterior and anteriorly to the body.

Figure 10:
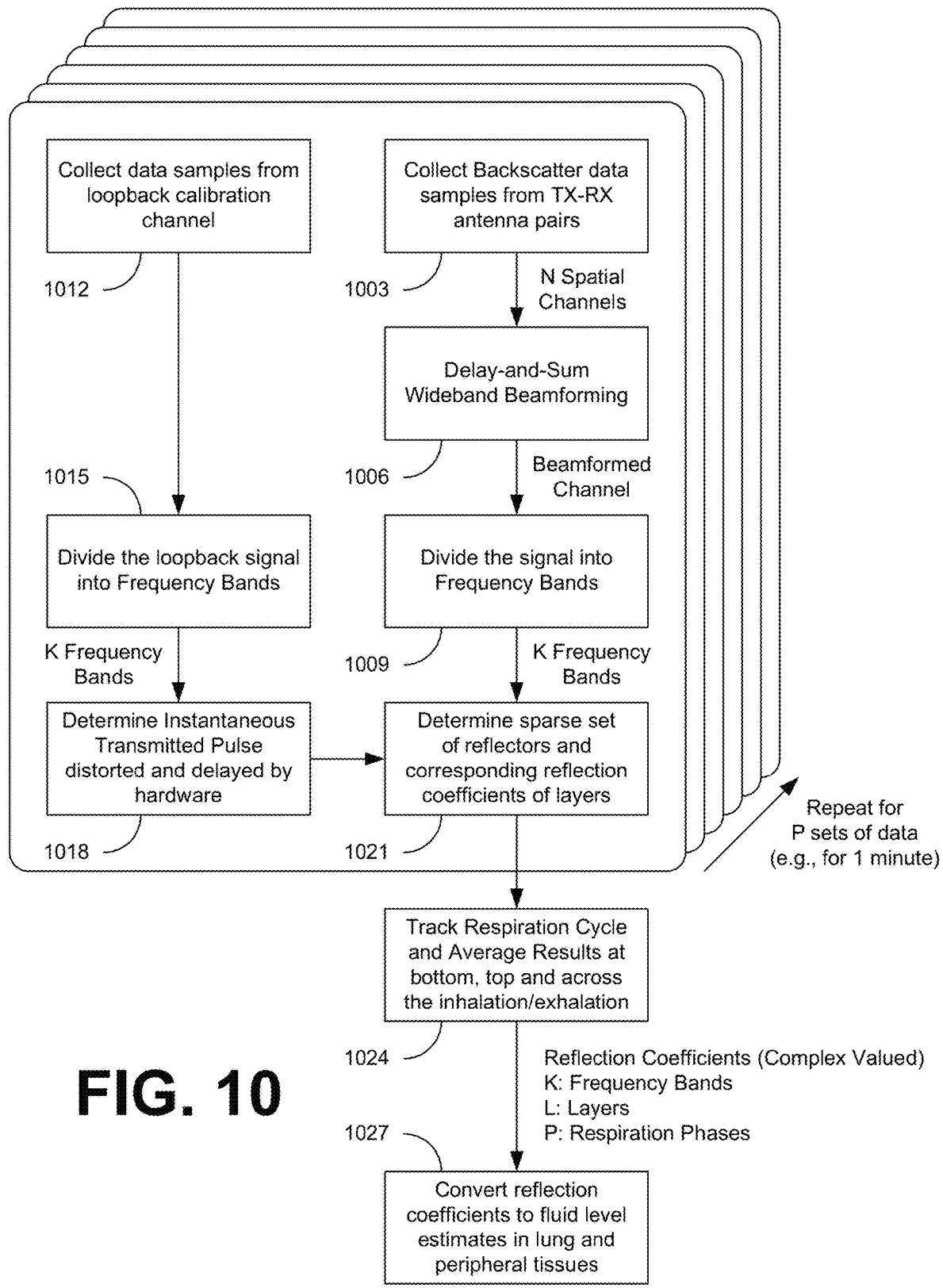
FIG. 10 is a flow chart illustrating an example of the operation of the bodily monitoring system of FIG. 1A, in accordance with various embodiments of the present disclosure.

Referring to FIG. 10, shown is a flow chart illustrating an example of the operation of the mobile bodily monitoring system 100. As previously discussed, the bodily monitoring system 100 comprises a UWB pulse generator 106 that generates UWB pulses for transmission into the tissue of the user 103, as shown in FIG. 1A. Beginning at 1003, backscatter data samples are collected using the TX-RX antenna pairs 109 in an UWB sensor positioned on the user's chest. The backscatter is collected for each of the N spatial channels for the TX-RX antenna pairs 109. The comprehensive sampling scheduler 118 can control the TX switching matrix 112 to direct a generated UWB pulse to each TX antenna, and control the RX switching matrix 115 to receive the reflected backscatter by the corresponding RX antenna in each pair. The captured backscatter data obtained from the different spatial channels by the UWB receiver 121 is delayed and summed by the DSP circuitry 127 (FIG. 1A) at 1006 to generate an averaged wideband beamformed signal, which is then divided into K frequency bands at 1009.

After completing the TX-RX cycle through each of the antenna pairs 109 at 1003, a UWB pulse can be directed from the UWB pulse generator 106 through the calibration circuit (or loop) at 1012 to obtain loopback measurements that can be used to account for distortion and delay produced by the hardware, and temperature effects. The measured calibration signal is then divided into the K frequency bands at 1015. Utilizing the frequency band information of the measured calibration signal, the computing device (or DSP circuitry) can determine the instantaneous UWB pulse that is distorted and delayed by the circuit hardware at 1018.

At 1021, the instantaneous UWB pulse can be used by the computing device (or DSP circuitry) to bootstrap the determination of a sparse set of reflectors and corresponding reflection coefficients for the tissue layers for the beamformed channel signal. Sparse deconvolution can be used to identify the UWB pulse shape and the reflection profiles for the K frequency bands as previously discussed. The reflection profiles for the frequency bands can be combined to determine an averaged reflection profiles. Use of the instantaneous UWB pulse determined at 1018 compensates for temperature effects on the UWB RF sensor during operation, which improves accuracy and consistency of the determined reflection profiles. The reflection coefficients can be extracted from the reflection profiles.

As shown in FIG. 10, the process (1003 through 1021) is repeated for each set of the N spatial channels for the TX-RX antenna pairs 109 multiple times over a defined period of time. For example, backscatter data samples (and a corresponding measurement through the calibration circuit) can be collected using the TX-RX antenna pairs 109 for a series of P transmitted pulses. The data can be collected for a predefined number of data sets or over a predefined period of time. With the reflection profiles and reflection coefficients determined for the P sets of backscatter data, the computing device can track the lung position and characteristics over the respiration cycle at 1024 based upon determined information. For example, the change in the depth of the lung tissue interface, as well as the lung tissue characteristics, produced by inhalation and exhalation can be determined for over the time period. The results that have been identified as being at the top of the inhalation or at the bottom of the exhalation can be averaged to provide a better measure of the lung tissue characteristics. In addition, results at a middle (or average) point during the breathing cycle can be determined and averaged to provide a common point for evaluation of the lung tissue.

At 1027, the reflection coefficients can be converted into fluid level estimates in the lung tissue. By using the averaged data at the bottom, top and middle of the respiration cycle, accuracy of the tissue locations and characteristics can be improved. In addition to lung tissue, information about peripheral tissues (e.g., skin, fat, muscle, bone and heart) can also be determined from the reflection coefficients. In some cases, correlations between the different tissues can be analyzed and evaluated. The information can be converted for display by the computing device in real time (or near real time).

As can be understood, processing of the backscatter data can be carried out by a combination of the DSP circuitry 127 (FIG. 1A) and the computing device. For example, the backscatter data and calibration measurement can be processed by the DSP circuitry to provide the frequency band information (1003 through 1015), which can then be transmitted to the computing device for subsequent processing and determination of the tissue information (1018 through 1027). In other implementations, additional processing can be carried out using the DSP circuitry 127 before transmission to the computing device.

Figure 11:
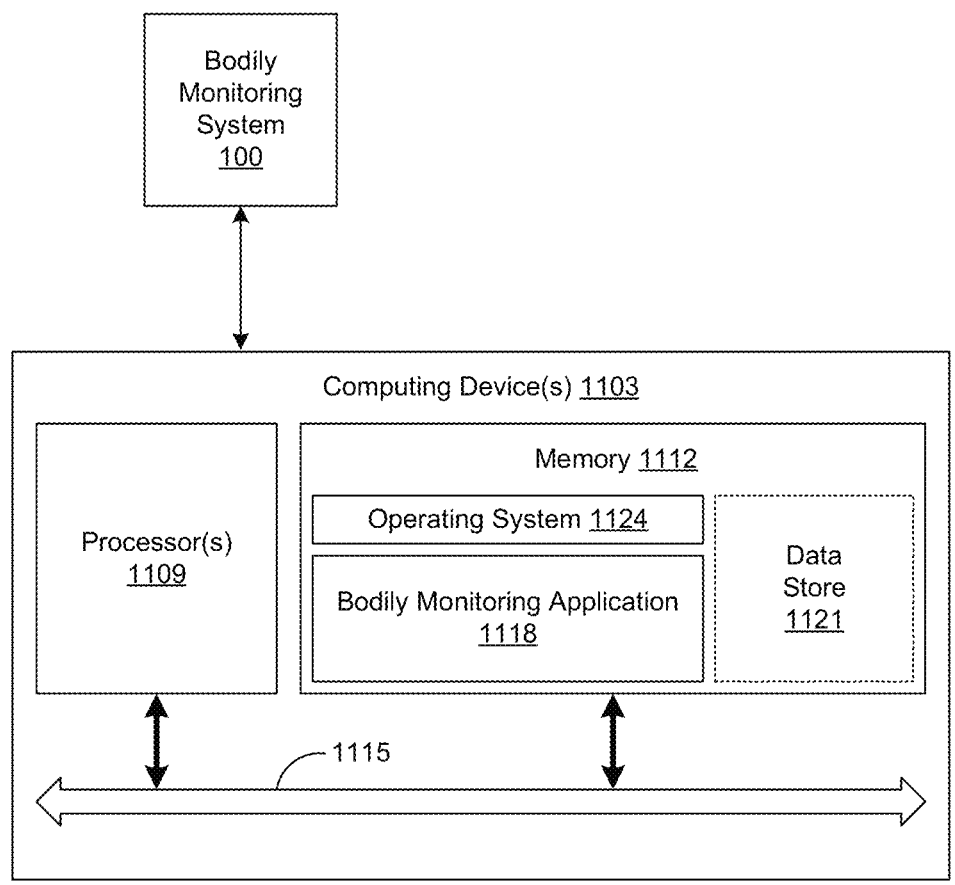
FIG. 11 illustrates an example of a computing device that can be used with the bodily monitoring system of FIG. 1A, in accordance with various embodiments of the present disclosure.

Referring now to FIG. 11, shown is an example of a computing device 1103 that can be included in the mobile bodily monitoring system 100. The computing device 1103 can be one or more computing device(s) 1103, which include at least one processor circuit, for example, having a processor 1109 and a memory 1112, both of which are coupled to a local interface 1115. To this end, the computing device(s) 1103 may comprise, for example, a computer, laptop, smartphone, tablet, or other mobile processing unit providing computing capability. The computing device(s) 1103 may include, for example, one or more display devices such as cathode ray tubes (CRTs), liquid crystal display (LCD) screens, gas plasma-based flat panel displays, LCD projectors, or other types of display devices, etc. The computing device(s) 1103 may also include, for example various peripheral devices. In particular, the peripheral devices may include input devices such as, for example, a keyboard, keypad, touch pad, touch screen, microphone, scanner, mouse, joystick, or one or more push buttons, etc. Even though the computing device 1103 is referred to in the singular, it is understood that a plurality of computing devices 1103 may be employed in the various arrangements as described above. The local interface 1115 may comprise, for example, a data bus with an accompanying address/control bus or other bus structure as can be appreciated.

Stored in the memory 1112 are both data and several components that are executable by the processor 1109. In particular, stored in the memory 1112 and executable by the processor 1109 are a bodily monitoring application 1118 and potentially other applications. Also stored in the memory 1112 may be a data store 1121 and other data. The data stored in the data store 1121, for example, is associated with the operation of the various applications and/or functional entities described below. For example, the data store may include data samples, reflective profiles, and other data or information as can be understood. In addition, an operating system 1124 may be stored in the memory 1112 and executable by the processor 1109. The data store 1121 may be may be located in a single computing device or may be dispersed among many different devices.

The bodily monitoring system 100 may be communicatively coupled to the computing device 1103 through a wireless communication link or network. In some embodiments, the bodily monitoring system 100 may be directly connected to the computing device 1103.

The components executed on the computing device 1103 include, for example, a bodily monitoring application 1118 and other systems, applications, services, processes, engines, or functionality not discussed in detail herein. It is understood that there may be other applications that are stored in the memory 1112 and are executable by the processor 1109 as can be appreciated. Where any component discussed herein is implemented in the form of software, any one of a number of programming languages may be employed such as, for example, C, C++, C#, Objective C, Java, Java Script, Perl, PHP, Visual Basic, Python, Ruby, Delphi, Flash, or other programming languages.

A number of software components are stored in the memory 1112 and are executable by the processor 1109. In this respect, the term "executable" means a program file that is in a form that can ultimately be run by the processor 1109. Examples of executable programs may be, for example, a compiled program that can be translated into machine code in a format that can be loaded into a random access portion of the memory 1112 and run by the processor 1109, source code that may be expressed in proper format such as object code that is capable of being loaded into a random access portion of the memory 1112 and executed by the processor 1109, or source code that may be interpreted by another executable program to generate instructions in a random access portion of the memory 1112 to be executed by the processor 1109, etc. An executable program may be stored in any portion or component of the memory 1112 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1112 is defined herein as including both volatile and nonvolatile memory and data storage components. Volatile components are those that do not retain data values upon loss of power. Nonvolatile components are those that retain data upon a loss of power. Thus, the memory 1112 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1109 may represent multiple processors 1109 and the memory 1112 may represent multiple memories 1112 that operate in parallel processing circuits, respectively. In such a case, the local interface 1115 may be an appropriate network that facilitates communication between any two of the multiple processors 1109, between any processor 1109 and any of the memories 1112, or between any two of the memories 1112, etc. The local interface 1115 may comprise additional systems designed to coordinate this communication, including, for example, performing load balancing. The processor 1109 may be of electrical or of some other available construction.

Although the bodily monitoring application 1118, and other various systems described herein, may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowchart of FIG. 10 shows functionality and operation of an implementation of portions of a bodily monitoring application 1118. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 1109 in a computer system or other system. The machine code may be converted from the source code, etc. If embodied in hardware, each block may represent a circuit or a number of interconnected circuits to implement the specified logical function(s).

Although the flowcharts of FIG. 10 shows a specific order of execution, it is understood that the order of execution may differ from that which is depicted. For example, the order of execution of two or more blocks may be scrambled relative to the order shown. Also, two or more blocks shown in succession in FIG. 10 may be executed concurrently or with partial concurrence. Further, in some embodiments, one or more of the blocks shown in FIGS. 3 and/or 6 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including bodily monitoring application 1118, that comprises software or code can be embodied in any non-transitory computer-readable medium for use by or in connection with an instruction execution system such as, for example, a processor 1109 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Figure 12A:
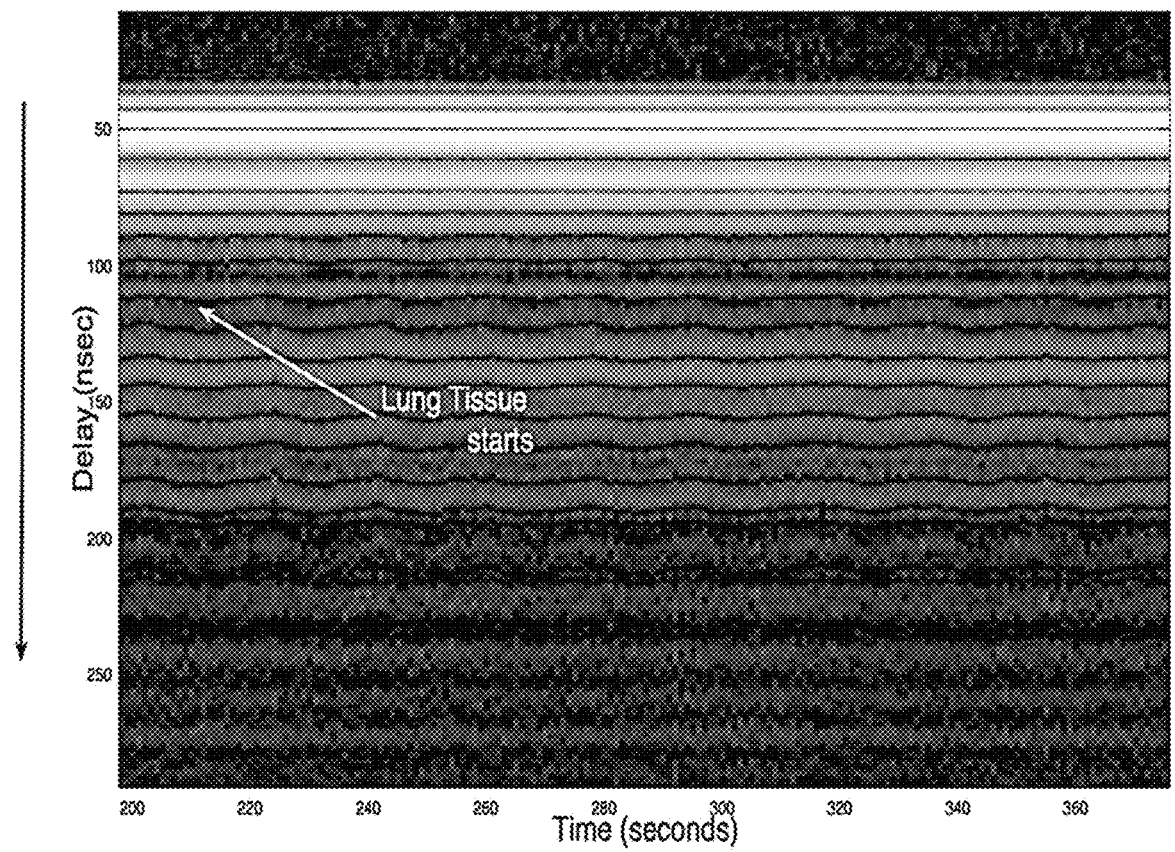
FIGS. 12A, 12B, 13 and 14A-14D illustrate examples of pilot study results using the bodily monitoring system of FIG. 1A, in accordance with various embodiments of the present disclosure.
Figure 12B:
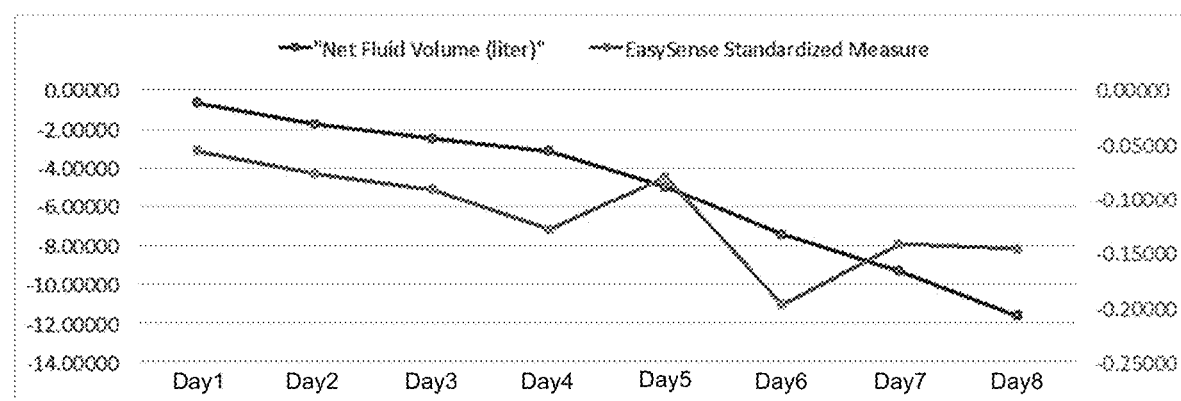

A pilot study of the mobile bodily monitoring system 100 has been conducted with patients having a primary diagnosis of acute decompensated heart failure. The patients were assessed with bodily monitoring technology in order to correlate thoracic fluid measurement with a clinical scenario of congestive heart failure. The mobile bodily monitoring system 100 is able to provide personalized measures to the patient, which can be used to help determine how close the patient is to a "dry" status. Fluid levels obtained by the bodily monitoring system 100 were compared to the total net fluid volume loss during hospitalization. Patients were assessed daily in order to correlate thoracic fluid measurement with clinical scenario of congestive heart failure. FIG. 12A shows a raw sensor readings captured as an image in which the depth of echo-producing interfaces is displayed along one axis with time (T) along the second axis; motion (M) of the tissue interfaces toward and away from the transducer (similar to TM mode of ultrasound). Note that the motion of the lung tissue due to respiration is visible and help to identify the relevant tissue transitions. FIG. 12B is a plot showing a comparison of the net fluid volume loss (in liters) to the standardized thoracic fluid measure provided by the mobile bodily monitoring system 100. The data was collected from the study subject over eight days.

Figure 13:
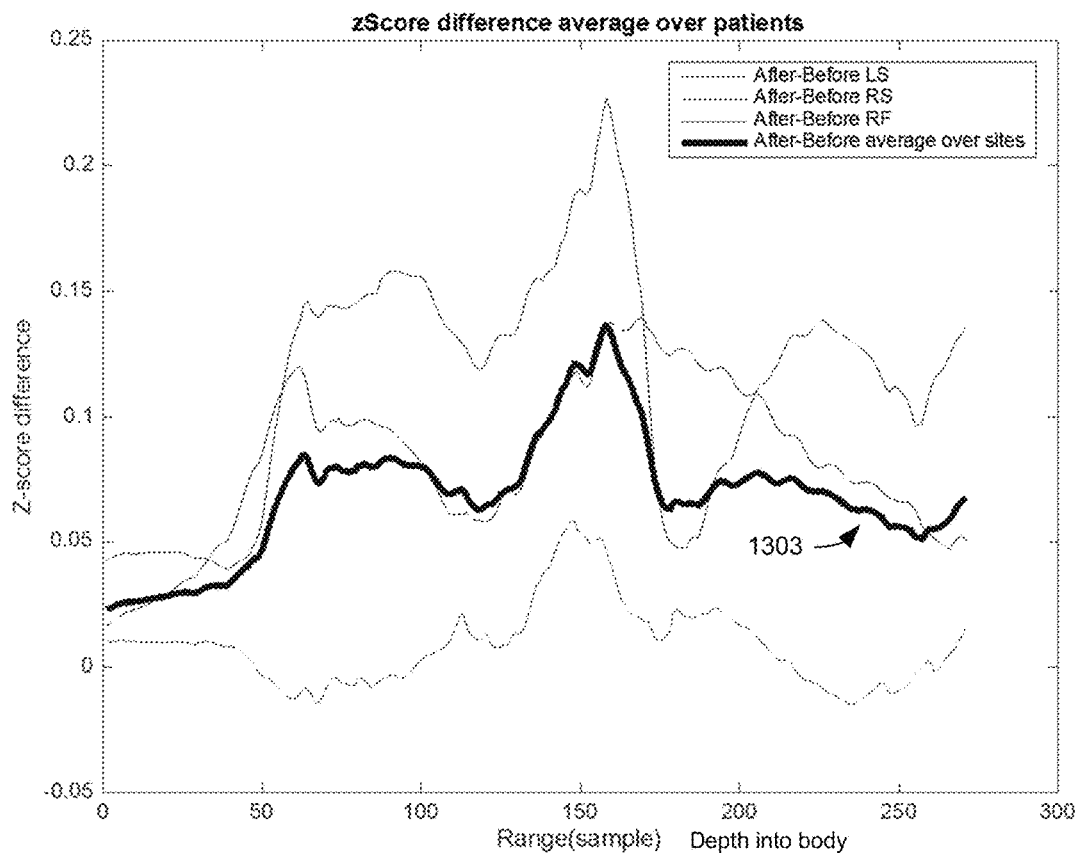
Figure 14A:
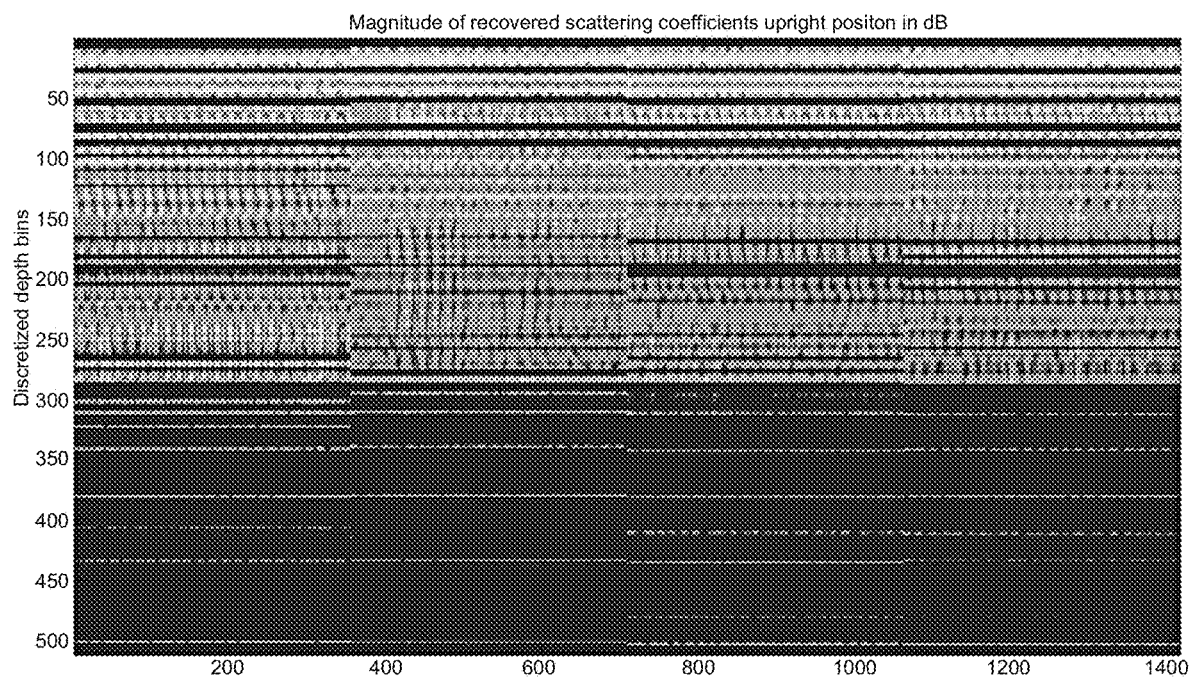
Figure 14B:
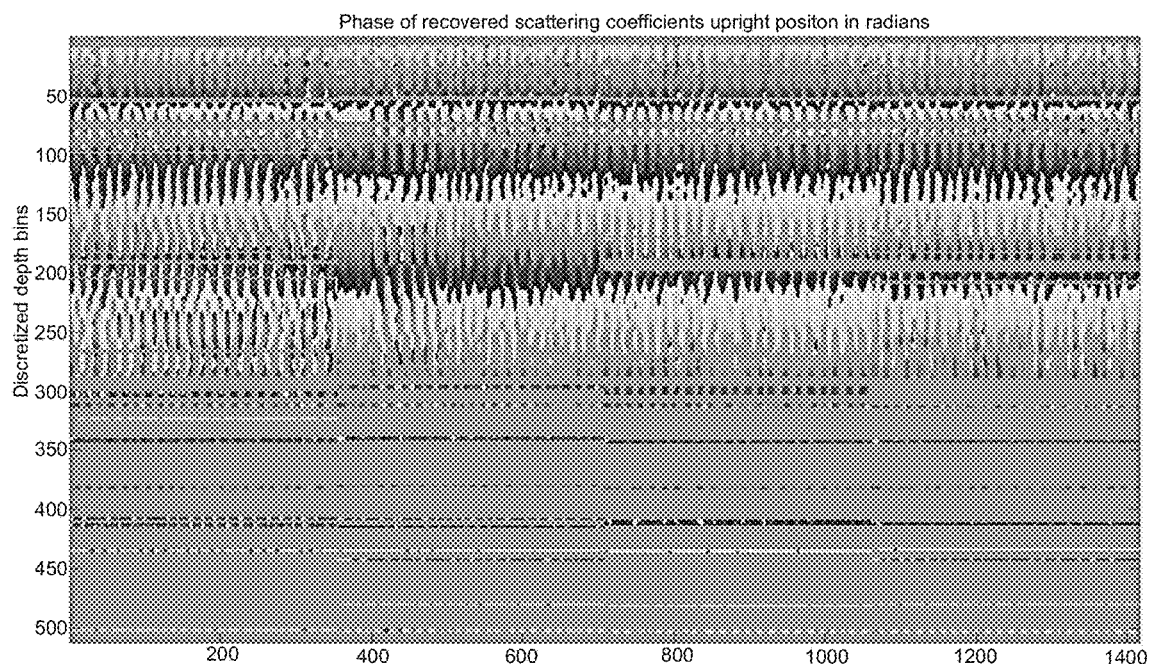
Figure 14C:
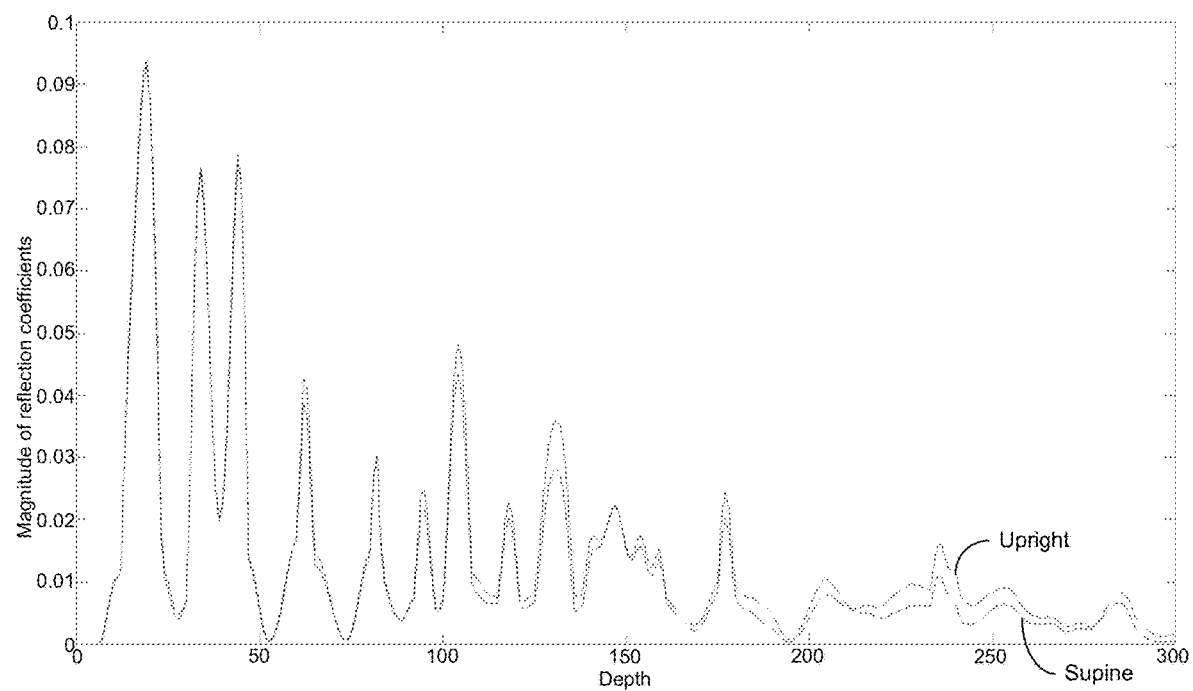
Figure 14D:
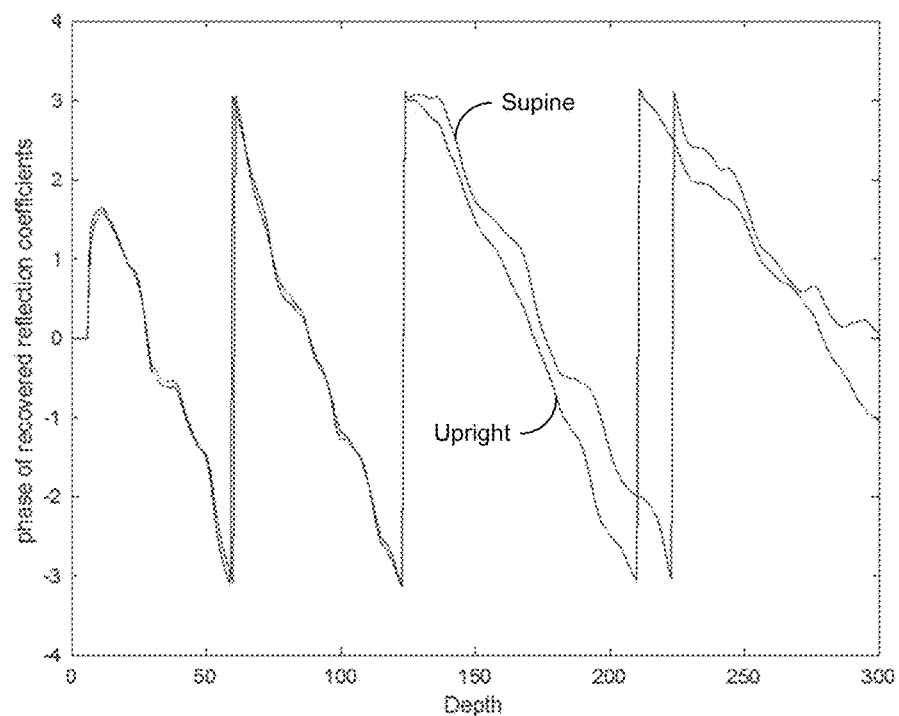

FIG. 13 shows a plot of an example of the average phase of the reflection coefficients over the depth (or range) into the body. Curve 1303 being above zero shows drying of the lungs especially at two compartments. Controlled repeated experiments were also carried out with a turntable. FIGS. 14A and 14B show the raw data of the backscatter magnitude and phase, respectively. The magnitude shows a layered structure of tissues, while the phase shows variation in time due to respiration. The recovered layered structure magnitude and phase for the average over respiration is plotted in FIGS. 14C and 14D, respectively. As can be seen, both the magnitude and phase shows changes in fluid levels deep in the body. The peaks and valleys of the respiration cycle can also be recovered.

Figure 15:
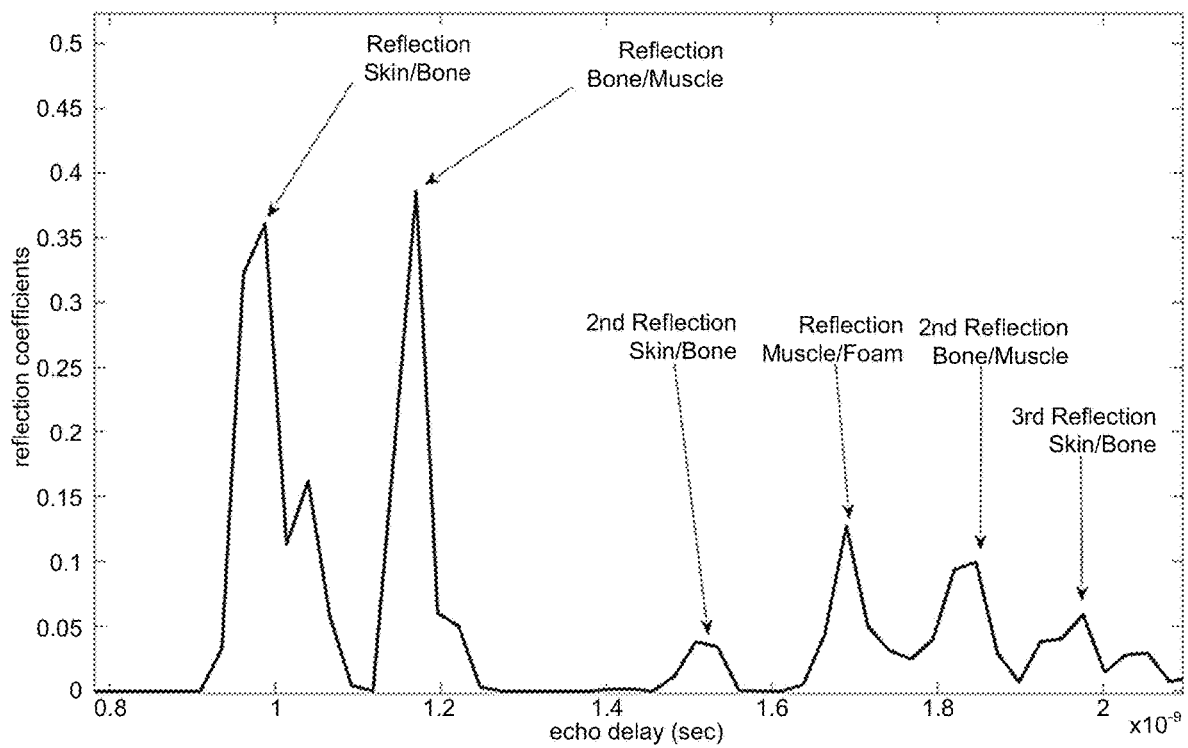
FIG. 15 illustrates an example of measured reflection coefficients using a multi-tissue phantom, in accordance with various embodiments of the present disclosure.

To test the validity of the measurements provided by mobile bodily monitoring system, a multilayer phantom consisting of three tissue layers (skin, bone, and muscle) was created and placed against a foam layer of known dielectric coefficient. The dielectric coefficient (permittivity and conductivity) of the emulated tissue layers were adjusted using polyethylene powder (PEP) and sodium chloride, respectively. Agar was used for self-shaping the mixture into solid layers, and a TX-151 powder was used to increase the mixture's viscosity. The dielectric constant of the emulated tissues were verified using an Agilent 85070E dielectric probe kit. The measured dielectric coefficients of the emulated tissue was compared against reference values and the measured conductivity and permittivity were found to be consistent with the reported values for these tissue types. FIG. 15 shows depth vs reflection amplitude measurements (similar to ultrasound A-mode). The observed delays and the reflection amplitudes can be used to estimate the dielectric properties of the multilayer tissue profile. For the three layers (skin, bone, muscle) the magnitude of the estimated dielectric coefficients were (41, 12, 55) with an average error of 4.5%.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A method for determining a bodily characteristic, comprising:
    collecting sets of reflected backscatter data for a sequence of ultra-wideband (UWB) pulses transmitted via an UWB sensor comprising an array of transmit (TX) and receive (RX) antenna pairs positioned on a body of a user, and a corresponding calibration measurement from a calibration channel in the UWB sensor;
    determining reflection coefficients for each of a plurality of tissue interfaces based on the sets of reflected backscatter data, the reflection coefficients determined from reflection profiles based upon the sets of reflected backscatter data for the sequence of UWB pulses and the corresponding calibration measurement, the reflection profile associated with a model of tissue layers in the body between the UWB sensor and lung tissue; and
    determining a fluid level content of the lung tissue based upon the reflection coefficients;
    wherein the sets of reflected backscatter data comprise reflected backscatter data obtained for each of the TX and RX antenna pairs in the UWB sensor that is combined to generate a wideband beamformed signal for each set of reflected backscatter data; and
    wherein the reflection profiles are determined based upon sparse deconvolution of the wideband beamformed signal of that set of reflected backscatter data using a compensated UWB pulse shape that is based upon the corresponding calibration measurement, wherein the compensated UWB pulse shape is compensated for temperature changes of the UWB sensor.

2. The method of claim 1, wherein the sparse deconvolution of the wideband beamformed signal is implemented for each of K frequency bands.

3. The method of claim 1, comprising:
    identifying a depth of a lung tissue interface at top, middle and bottom points in a respiration cycle of the lung tissue based upon the reflection coefficients; and
    where determining the fluid level content of the lung tissue comprises determining fluid level content at the top, middle and bottom points in the respiration cycle.

4. The method of claim 1, comprising determining characteristics of actual tissue layers located between the UWB sensor and the lung tissue.

5. The method of claim 4, wherein the characteristics of the actual tissue layers comprise a location of at least one actual tissue layer interface or a dielectric property of at least one actual tissue layer.

6. A mobile bodily monitoring system, comprising:
an ultra-wideband (UWB) sensor comprising an array of antennas comprising pairs of transmit (TX) and receive (RX) antennas, and a calibration channel, the UWB sensor configured to be positioned on a body of a user;
a radio frequency (RF) front end comprising a UWB pulse generator coupled to the TX antennas of the array of antennas and a UWB receiver coupled to the RX antennas of the array of antennas, where UWB pulses generated by the UWB pulse generator are sequentially transmitted into the body of the user through the TX antennas and reflected backscatter signals are received through the RX antenna of the pair of TX and RX antennas;
a wireless transmitter configured to communicate data associated with the reflected backscatter signals and a corresponding calibration measurement from the calibration channel; and
a computing device configured to receive the data associated with the reflected backscatter signals and determine bodily characteristics of the user based upon the reflected backscatter signals and the corresponding calibration measurement;
wherein the computing device is configured to:
determine a reflection profile based upon the data associated with the reflected backscatter signals and the corresponding calibration measurement for the sequence of transmitted UWB pulses, the reflection profile associated with a model of tissue layers in the body between the UWB sensor and a target tissue,
determine reflection coefficients based upon the reflection profile; and
determine characteristics of the target tissue from generated target tissue data;
wherein the characteristics of the target tissue comprise depth of an interface with the target tissue or dielectric properties of the target tissue;
wherein the target tissue is lung tissue;
wherein the reflection profile is determined through sparse deconvolution of an averaged wideband backscatter signal based upon the data associated with the reflected backscatter signals for the sequence of UWB pulses, using a compensated UWB pulse shape that is based upon the corresponding calibration measurement wherein the compensated UWB pulse shape is compensated for temperature changes of the UWB sensor.

7. The mobile bodily monitoring system of claim 6, wherein the computing device is configured to identify a measure of lung fluid content based upon the characteristics of the lung tissue.

8. The mobile bodily monitoring system of claim 7, wherein the computing device is configured to concurrently identify one or more of heart rate, heart rate variability, respiration rate or tidal volume.

9. The mobile bodily monitoring system of claim 6, wherein the computing device is configured to identify top and bottom depths of a lung tissue interface over a respiration cycle of the lung tissue.

10. The mobile bodily monitoring system of claim 9, wherein the computing device is configured to identify the dielectric properties at the top and bottom depths and at an average depth in the respiration cycle of the lung tissue.

11. The mobile bodily monitoring system of claim 6, wherein the computing device is configured to determine the reflection profile for each of a series of reflected backscatter data sets, each of the reflected backscatter data sets comprising data associated with the reflected backscatter signals for the sequence of transmitted UWB pulses associated with the set.

12. The mobile bodily monitoring system of claim 6, wherein the calibration channel comprises a temperature calibration loop having a load of known impedance positioned adjacent to the array of antennas.

13. The mobile bodily monitoring system of claim 12, wherein variations in the transmitted UWB pulses are compensated for based upon the corresponding calibration measurement.

14. The mobile bodily monitoring system of claim 6, comprising digital signal processing (DSP) circuitry configured to obtain and process the reflected backscatter signals and the corresponding calibration measurement for transmission to the computing device.

15. The mobile bodily monitoring system of any of claim 6, wherein the UWB pulses are transmitted into the body at a rate of 10,000 per second.

* * * * *